US007038110B1

(12) United States Patent
Yano et al.

(10) Patent No.: US 7,038,110 B1
(45) Date of Patent: May 2, 2006

(54) PHOTOSENSITIVITY GENE OF PLANT AND UTILIZATION THEREOF

(75) Inventors: Masahiro Yano, Tsukuba (JP); Takuji Sasaki, Tsukuba (JP); Yuji Takahashi, Tsukuba (JP)

(73) Assignees: National Institute of Agrobiological Sciences, Ibaraki (JP); Society for Techno-Innovation of Agriculture, Forestry and Fisheries, Tokyo (JP); National Agriculture and Bio-Oriented Research Organization, Saitama (JP)

( * ) Notice: Subject to any disclaimer, the term of this patent is extended or adjusted under 35 U.S.C. 154(b) by 116 days.

(21) Appl. No.: 10/129,357

(22) PCT Filed: Nov. 1, 2000

(86) PCT No.: PCT/JP00/07692

§ 371 (c)(1),
(2), (4) Date: Oct. 8, 2002

(87) PCT Pub. No.: WO01/32880

PCT Pub. Date: May 10, 2001

(30) Foreign Application Priority Data

Nov. 2, 1999  (JP) ................................. 11-312589

(51) Int. Cl.
*C12N 15/29* (2006.01)
*C12N 15/82* (2006.01)
*C12N 15/87* (2006.01)
*C12N 5/04* (2006.01)
*A01H 5/00* (2006.01)

(52) U.S. Cl. ...................... 800/278; 800/298; 800/290; 800/320.2; 536/23.6; 435/410; 435/320.1; 435/419; 435/468

(58) Field of Classification Search ............... 536/23.1, 536/23.6; 435/320.1, 419, 468, 410; 800/298, 800/278, 290, 320.2
See application file for complete search history.

(56) References Cited

U.S. PATENT DOCUMENTS 5,859,326 A * 1/1999 An .............................. 800/290

FOREIGN PATENT DOCUMENTS

| CA | 2201927 | 5/1996 |
|---|---|---|
| EP | 1 229 119 A1 | 8/2002 |
| WO | WO 01/32881 A1 | 5/2001 |
| WO | WO 03/100062 A1 | 12/2003 |

OTHER PUBLICATIONS

Kano-Murakami et al (1993, FEBS 334:365-368).*
MacDonald et al (2003, Cell 113:671-672).*
Bowie et al, Science 247:1306-1310, 1990.*
McConnell et al, Nature 411 (6838):709-713, 2001.*
Peracchia et al (1999, Plant Molecular Biology 40:199-211).*
Database EMBL 'Online, Nov. 2, 1998, Peracchia, G. et al, "Z. mays mRNA for Casein Kinase II Alpha Subunit," retrieved from EBI Database accession No. Y11526, XP002300053.
Kato, K. et al., "Comparative Mapping of the Wheat *Vrn-A1* Region with the Rice *Hd-6* Region," *Genome*, Ottowa, Canada, Apr. 1999, 42(2):204-209, XP008020108.
Yamamoto, T. et al., "Identification of Heading Date Quantiative Trait Locus *Hd6* and Characterization of Its Epistatic Interactions With *Hd2* in Rice Using Advanced Backcross Progeny," *Genetics*, Feb. 2000, 154(2):885-891, XP002300052.
Takahashi, Y. et al., "*Hd6*, a Rice Quantitative Trait Locus Involved in Photoperiod Sensitivity, Encodes the α Subunit of Protein Kinase CK2," *Proceedings of the National Academy of Sciences of USA, National Academy of Science.*, Washington, US., Jul. 3, 2001, 98(14):7922-7927, XP002970467.
Dobrowolska, G., et al., "Cloning and Sequencing of the Casin Kinase 2 α Subunit from Zea Mays," *Biochimica et Biophysica Acta,* 1129(1):139-140, Dec. 2, 1991.
Mizoguchi, T. et al., "Cloning and Characterization of Two cDNAs Encoding Casein Kinase II Catalytic Subunits in *Arabidopsis thaliana,*" *Plant Mol. Biol.,* 21(2):279-289, Database Medline, No. 93144703, 1993.
Tsai, K., "Studies on Earliness Genes in Rice with Special Reference to Analysis of Isoalleles at E Locus," *Japanese J. of Genetics*, 52(2):115-128, Apr. 25, 1976.
Yokoo, M. et al., "Tight Linkage of Blast-Resistance with Late Maturity Observed in Different Indica Varieties of Rice," *Japan. J. Breed.*, 21(1):35-39, 1971.
Okumoto, Y. et al., "Analysis of a Rice Variety Taichung 65 and its Isogenic Early-Heading Lines for Late-Heading Genes $E_1$, $E_2$, and $E_3$," *Japan. J. Breed.,* vol. 42, pp. 415-429, 1992.
Okumoto, Y. et al., "No. 120: Location of the Late Heading-Time Gene Locus E3," *Japan. J. of Breeding*, vol. 47, Supp 1:31, Abstracts of the $91^{st}$ Annual Meeting of Japan Society of Breeding.

(Continued)

*Primary Examiner*—David T. Fox
*Assistant Examiner*—Stuart F. Baum
(74) *Attorney, Agent, or Firm*—Seed IP Law Group, PLLC

(57) ABSTRACT

The present inventors successfully isolated a photoperiod sensitivity gene Hd6 from rice by a linkage analysis. It was revealed that the photoperiod sensitivity of plants can be modified by introducing the gene or controlling the expression of the gene. Further, it was demonstrated that the photoperiod sensitivity of plants can be assessed by detecting the presence or absence of the functional gene.

12 Claims, 15 Drawing Sheets

OTHER PUBLICATIONS

Yamagat, H. et al., "Analysis of Genes Controlling Heading Time in Japanese Rice," *Rice Genetics*, pp. 351-359, 1986.

Yamamoto, T. et al., "Fine Mapping and Characterization of Quantitative Trait Loci of Heading Date in Rice," in *Proceedings of the Plant Genome IV Conference*, San Diego, CA, Jan. 1995, p. 124.

Okumoto, Y. et al., "Genotypic Difference in Response to Light Interruption in Japanese Rice Varieties," *Rice Genetics*, pp. 778-780, 1991.

Kramer, W. et al., "Oligonucleotide-Directed Construction of Mutations via Gapped Duplex DNA," Methods in Enzymology, vol. 154, pp. 350-367, 1987.

Southern, E., "Detection of Specific Sequences Among DNA Fragments Separated by Gel Electrophoresis," *J. Mol. Biol.*, 98(3):503-517, 1975.

Saiki, R. et al., "Enzymatic Amplification of β-Globin Genomic Sequences and Restriction Site Analysis for Diagnosis if Sickle Cell Anemia," *Science*, vol. 230, pp. 1350-1354, 1985.

Saiki, R. et al., "Primer-Directed Enzymatic Amplification of DNA with a Thermostable DNA Polymerase," *Science*, vol .239, pp. 487-491, 1988.

Mandel, M., "Calcium-Dependent Bacteriophage DNA Infection," *J. Mol. Biol.*, vol. 53, pp. 159-162, 1970.

Hanahan, D., "Studies on Transformation of *Escherichia coli* with Plasmids," *J. Mol. Biol.*, 166(4):557-580, 1983.

Ecker, J. et al., "Inhibition of Gene Expression in Plant Cells by Expression of Antisense RNA," *Proc. Natl. Acad. Sci. USA*, vol. 83, pp. 5372-5376, Aug. 1986.

van der Krol, A. et al., "An Anti-Sense Chalcone Synthase Gene in Transgenic Plants Inhibits Flower Pigmentation," *Nature*, vol. 333, pp. 866-869, 1988.

Hirashima, A. et al., "7. Regulation of Gene Expression by Antisense RNA," pp. 319-347, 1993.

Koizumi, M. et al., "Ribozyme for Sequence-Dependent Cleavage of Target RNA," *Tanpakushitsu Kakusan Kosho*, vol. 35, pp. 2191-2200, 1990.

Koizumi, M. et al., "Construction of Series of Several Self-Cleaving RNA Duplexes using Synthetic 21-mers," *FEBS Letters*, 228(2):228-230, Feb. 1988.

Koizumi, M. et al., "Cleavage of Specific Sites of RNA Designed Ribozymes," *FEBS Letters*, 239(2):285-288, Nov. 1988.

Koizumi, M. et al., "Design of RNA Enzymes Distinguishing a Single Base Mutation in RNA," *Nucleic Acids Research*, 17(17):7059-7071, 1989.

Buzayan, J. et al., "Non-enzymatic Cleavage and Ligation of RNAs Complementary to a Plant Virus Satellite RNA," *Nature*, vol. 323, pp. 349-353, Sep. 1986.

Kikuchi, Y, et al., "Site-Specific Cleavage of Natural mRNA Sequences by Newly Designed Hairpin Catalytic RNAs," *Nucleic Acids Research*, 19(24):6751-6755, 1991.

Kikuchi, Y., "Ribozymes: Types in vivo Activitiy—Hammerhead and Hairpin Ribozymes," *Kagaku and Seibutsu*, 30(2):112-118, 1992.

Taira, K. et al., "Construction of A Novel Artificial-Ribozyme-Releasing Plasmid," *Protein Engineering*, 3(8): 733-737, 1990.

Dzianott, A. et al., "Derivation of an Infectious Viral RNA by Autolytic Cleavage of in Vitro Transcribed Viral cDNAs," *Proc. Natl. Acad. Sci. USA*, 86(13):4823-4827, Jul. 1989.

Grosshans, C. et al., "A Hammerhead Ribozyme Allows Synthesis of a New Form of the Tetrahymena Ribozyme Homogenous in Length with a 3' end Blocked for Transesterification," *Nucleic Acids Research*, 19(14):3875-3880, 1991.

Taira, K. et al., "Construction of a Novel RNA-Transcription-Trimming Plasmid which can be used both in vitro in place of run-off and (G)-Free Transcriptions and in vivo as Multi-Sequences Transcription Vectors," Nucleic Acids Research, 19(19):5125-5130, 1991.

Yuyama, N. et al., "Construction of a tRNA-Embedded-Ribozyme Trimming Plasmid," *Biochem. and Biophys. Res. Comm.*, 186(3):1271-1279, Aug. 14, 1992.

Smyth, D., "Gene Silencing: Cosuppression at a Distance," *Current Biology*, 7(12):R793-R795, 1997.

Martienssen, R., "Epigenetic Phenomena: Paramutation and Gene Silencing in Plants," *Current Biologyu*, 6(7):810-813, 1996.

Toki, S. et al., Expression of a Maize Ubiquitin Gene Promoter-bar Chimeric Gene in Transgenic Rice Plants, *Plant Physiol.*, vol. 100, pp. 1503-1507, 1992.

Datta, S.K., "8 Polyethylene-Glycol-Medicated Direct Gene Transfer to Indica Rice Protoplasts and Regeneratiion of Transgenic Plants," pp. 66-74, 1995.

Christou, P. et al., "Production of Transgenic Rice (Oryza Sativa L.) Plants from Argonomically Important Indicia and Japonica Varieties via Electric Discharge Particle Acceleration of Exogenous DNA into Immature Zygotic Embryos," *Bio/Technology*, vol. 9, pp. 957-962, Oct. 1991.

Hiei, Y. et al., "Efficient Transformation of Rice (Oryza Sativa L.) Mediated by Agrobacterium and Sequence Analysis of the Boundaries of the T-DNA," *The Plant Journal*, 6(2):271-282, 1994.

Neff, M. et al., "dCAPS, A Simple Technique for the Genetic Analysis of Single Nucleotide Polymorphisms: Experimental Applications in *Arabidopsis thaliana* Genetics," *The Plant Journal*, 14(3):387-392, 1998.

Wu, D. et al., "Allele-Specific Enzymatic Amplification of βGlobin Genomic DNA for Diagnosis of Sickle Cell Anemia," *Proc. Natl. Acad. Sci. USA*, 86(8):2757-2760, Apr. 1989.

Konieczny, A et al., "A procedure for Mapping Arabidopsis Mutations Using Co-Dominant Ecotype-Specific PCR-Based Markers," *The Plant Journal*, 4(2):403-410, 1993.

Mannerlof, M. et al., "Screening of Transgenic Plants by Multiplex PCR," *Plant Mol. Biol. Reporter*, 15(1):38-45, 1997.

Lee, Y. et al., "Antisense Expression of the CK2 α-Subunit Gene in Arabidopsis. Effects on Light-Regulated Gene Expression and Plant Growth," *Plant Physiol.*, 119(3):989-1000, 1999.

Sugano, S. et al., "Protein Kinase CK2 Interacts with and Phosphorylates the Arabidopsis Circadian Clock-Associated 1 Protein," *Proc. Natl. Acad. Sci. USA*, 95(18):11020-11025, Sep. 1998.

English Translation of: Hayashi, H. et al., "Ine Kankousei Hd-2 to Hd-6 no Idenshi Hatsugen ni Okeru Sougo Sayou," *Breeding Science*, 48(1):70, 1998.

English Translation of: Katou, K., "Shussuibi ni Kanyo Suru Komugi Vrnl Ryouiki to Ine Hd-6 Ryouiki Tono Hikaku Chizu," *Breeding Science*, 48(1):98, 1998.

* cited by examiner

```
Nipponbare -1096:                                         CACACTATTGGCCTGGC -1080
Kasalath   -1097:                                         CACACTATTGGCCTGGC -1081
                                                          *****************

Nipponbare -1079: CTTAGTGCCAGAACCTGTTTATTTCTTCTGTTTTATAGTCTGATGCATTTTTGTTAATGG -1020
Kasalath   -1080: CTTAGTGCCAGAACCTGTTTATTTCTTCTGTTTTATAGTCTGATGCATTTTTGTTAATGG -1021
                  ************************************************************

Nipponbare -1019: AAATGGAGGGCCTTTTTCCCTTCGATAAAAAAAATGTATAAGATTATTAGTTAATTATGG -960
Kasalath   -1020: AAATGGAGGGCCTTTTTCCCTTCGATAAAAAAAATGTATGAGATTATTAGTTAATTATGG -961
                  ***************************************  *******************

Nipponbare -959: TAGTATTGAAAAATATACCACGAT-AAAAAAACTTAAAATCAAATTAAAATTAAGTTTCA -901
Kasalath   -960: TAGTATTGAAAAATATACCACGATAAAAAAAACTTAAAATCAAATTAAAATTAATTTTCA -901
                 ************************ *******************************  ****

Nipponbare -900: ACATTTATATTTTAGCTACGGGTGATAAGTCAAAACACAAACAACGGTCTTTGTACGTAA -841
Kasalath   -900: ACATTTATATTTTAGCTACGGGTGATAAGTCAAAACACAAACAACGGTCTTTGTACGTAA -841
                 ************************************************************

Nipponbare -840: GTCTTTTTCAAAACTTGTGGTAAACATTCTCCGTTCAGTTATTAATATTTGATGTTTAGG -781
Kasalath   -840: GTCTTTTTCAAAACTTGTGGTAAACATTCTTCGTTCAGTTATTAATATTTGATGTTTAGG -781
                 ****************************** *****************************

Nipponbare -780: ACAAGATCCGATCAAACTTCTAAAATTCTAACAAATCAATTCTATATTAAATTAAGTTTA -721
Kasalath   -780: ACAAGATCTGATCAAACTTCTAAAATTCTAACAAATCAATTCCATATTAAATTAAGTTTA -721
                 ********  ******************************** *****************

Nipponbare -720: TGAAGCGCTATAAGCTTGTGATTTTATGATAGCACTTGTTGAGATAAATATATGTATATC -661
Kasalath   -720: TGAAGCGCTATAAGCTTGTGATTTTATGATAGCACTTGTTGAGATAAATATATGTATATC -661
                 ************************************************************

Nipponbare -660: TTTTATCTTATCTTTAAACTAAGTAGAGGTATTTGTTAAATTATTGATGATCAGAAATTT -601
Kasalath   -660: TTTTATCTTATCTTTAAACTAAGTAGAGGTATTTGTTAAATTATTGATGATCAGAAATTT -601
                 ************************************************************

Nipponbare -600: AAAAAGTTCGACCATATCTTGTACTAGTACTAAACGTAAAATATTTTTGACTAAAGGAAG -541
Kasalath   -600: AAAAAGTTCGACCATATCTTGTACTAGTACTAAACGTAAAATATTTTTGACTAAAGGAAG -541
                 ************************************************************

Nipponbare -540: TAATTAAAATTTAAGAGGCAAAATTACGTGTGAATTTGAGAAGACTTCCAATTCAACAGC -481
Kasalath   -540: TAATTAAAATTTAAGAGGCAAAATTACGTGTGAATTTGAGAAGACTTCCAATTCAACAGC -481
                 ************************************************************

Nipponbare -480: TCAATGATCGGGACACATTCTTAAAAAAGAAAAAAAAGAAACAAAAAAGATCCGGACACG -421
Kasalath   -480: TCAATGATCGGGACACATTCTTAAAAAAGAAAAAAAAGAAACAAAAAAGATCCGGACACG -421
                 ************************************************************

Nipponbare -420: CATGCGCAAATGGAGCTTTCATAGGCAGAAGGCGTAATCAACTGGAAGGCGTCTTCTCCT -361
Kasalath   -420: CATGCGCAAATGGAGCTTTCATAGGCAGAAGGCGTAATCAACTGGAAGGCGTCTTCTCCT -361
                 ************************************************************

Nipponbare -360: GGAGGGAAAGGTCGGGCCCACGTAAGGGAACAAAACCACCTGTCAGTGACCAAAAGCCAG -301
Kasalath   -360: GGAGGGAAAGGTCGGGCCCACGTAAGGGAACAAAACCACCTGTCAGTGACCAAAAGCCAG -301
                 ************************************************************

Nipponbare -300: CAGATTCCAGAGTCGCCGTCCCACGCCGCCTCTATCTATCTCCACGTGAAATAAAAAAAA -241
Kasalath   -300: CAGATTCCAGAGTCGCCGTCCCACGCCGCCTCTATCTATCTCCACGTGAAATAAAAAAAA -241
                 ************************************************************
```

*FIG. 4A*

```
                                        First exon
Nipponbare  -240:AACAAAGCTCCCGAAAATATTCTCTCTCCCCCACCCCCGAAACCCTAGCGCGACCTCGCC -181
Kasalath    -240:AACAAAGCTCCCGAAAATATTCTCTCTCCCCCACCCCCGAAACCCTAGCGCGACCTCGCC -181
                 ************************************************************

Nipponbare  -180:GCCGGCAATGGCCGCATGACCGATGCGCCTCCGCCGAGGAGCCGCCCGCACCCACCCAGC -121
Kasalath    -180:GCCGGCAATGGCCGCATGACCGATGCGCCTCCGCCGAGGAGCCGCCCGCACCCACCCAGC -121
                 ************************************************************

Nipponbare  -120:AGCAGCGTCGCCGTGCCCGCCGCCGCGGCGGCAGTGATCGCAGCCGCCCTCGCGTCCTCC -61
Kasalath    -120:AGCAGCGTCGCCGTGCCCGCCGCCGCGGCGGCAGTGATCGCAGCCGCCCTCGCGTCCTCC -61
                 ************************************************************

Nipponbare   -60:TTCCTCGCCCTGCTGCAGCCGCCCCGGCGCGCCCCGGTCGCCGCGGGATCCAGGGTCGGC -1
Kasalath     -60:TTCCTCGCCCTGCTGCAGCCGCCCCGGCGCGCCCCGGTCGCCGCGGGATCCAGGGTCGGC -1
                 ************************************************************

Nipponbare     1:ATGTCGAAGGCGAGGGTCTACGCCGACGTCAACGTGCTGCGCCCCAAGGAGTACTGGGAC 60
Kasalath       1:ATGTCGAAGGCGAGGGTCTACGCCGACGTCAACGTGCTGCGCCCCAAGGAGTACTGGGAC 60
                 ************************************************************
                 Initiation codon
Nipponbare    61:TACGAGGCGCTCACCGTTCAATGGGGGTAGGTAGCACAGCCAGCCAGCTGACGTCACCTT 120
Kasalath      61:TACGAGGCGCTCACCGTTCAATGGGGGTAGGTAGCACAGCCAGCCAGCTGACGTCACCTT 120
                 ************************************************************
                                                     First intron
Nipponbare   121:CCTGAGCCCCCTGATCAGCGGCCGTAGCTTGTATTCTCCAGATTTAGTTCGCGATCCGTA 180
Kasalath     121:CCTGAGCCCCCTGATCAGCGGCCGTAGCTTGTATTCTCCAGATTTAGTTCGCGATCCGTA 180
                 ************************************************************

Nipponbare   181:TCCCGTACACCTGGGCTGGGTTTGCTTATTGGGATTAGGTTGGATTATTGGGTTATGCGT 240
Kasalath     181:TCCCGTACACCTGGGCTGGGTTTGCTTATTGGGATTAGGTTGGATTATTGGGTTATGCGT 240
                 ************************************************************

Nipponbare   241:AGGTTTGCTTGTGCCTGTAGATTTTGGTTTTGGTCAGGGAATTGGGAATTTATTGTAGCT 300
Kasalath     241:AGGTTTGCTTGTGCCTGTAGATTTTGGTTTTGGTCAGGGAATTGGGAATTTATTGTGGCT 300
                 ********************************************************* ***

Nipponbare   301:TGAAGGTTAGATTGAATTGCTTCTGTTTCTATTAGGACGAACTCAATACCGAAGACTGCT 360
Kasalath     301:TGAAGGTTAGATTGAATTGCTTCTGTTTCTATTAGGACGAACTCAATACCGAAGACTGCT 360
                 ************************************************************

Nipponbare   361:TTGGTAGTTTTACATGTTTGTACTATAGGAGTAGGGGACACATGTTTACCGAATGGTTGA 420
Kasalath     361:TTAGTAGTTTTACATGTTTGTACTATAGGAGTAGGGGACACATGTTTACCGAATGGTTGA 420
                 ** *********************************************************

Nipponbare   421:AGAAATTGTTATGAATTTGCAAGGTTATGATTTTAATTTTGGAATCAATCTCACTATATC 480
Kasalath     421:AGAAACTGTTATGAATTTGCAAGGTTATGATTTTAATTTTGGAATCAATCTCACTATATC 480
                 ***** ******************************************************

Nipponbare   481:TTCCTTTTAAAGTTGATACTAGTGTTGTTCAGTTAAGAGCCTTTGTTTGATTGTGAATGG 540
Kasalath     481:TTCCTTTTAAAGTTGATACTAGTGTTGTTCAGTTAAGAGCCTTTGTTTGATTGTGAATGG 540
                 ************************************************************

Nipponbare   541:CAAGCTGTAGGTATTGATCCTATTTTTGTTGGGGATAAAATCTAAGTTAAGGCAAAATTA 600
Kasalath     541:CAAGCTGTAGGTATTGATCCTATTTTTGTTGGGGATAAAATCTAAGTTAAGGCAAAATTA 600
                 ************************************************************

Nipponbare   601:GGCAGTTTTATGTTTAATCATTGGAACAAAGTAAGTTGGTGATGGGTTTCTGGGTGTTTC 660
Kasalath     601:GGCAGTTTTATGTTTAATCATTGGAACAAAGTAAGTTGGTGATGGGTTTCTGGGTGTTTC 660
                 ************************************************************
```

*FIG. 4B*

| | | |
|---|---|---|
| Nipponbare | 661: | TTTTGCATCATCTGATAACCAAGATTGATGAGTAAAGCATAACTTGGTAGTATAGTGCTT 720 |
| Kasalath | 661: | TTTTGCATCATCTGATAACCAAGATTGATGAGTAAAGCATAACTTGGTAGTATAGTGCTT 720 |
| | | ************************************************************ |
| Nipponbare | 721: | TGGGCCTAATCTTCTTTAGCACTGAACATTCACCAAGTTCTATGCTTTTATGTAATCTCA 780 |
| Kasalath | 721: | TGGGCCTAATCTTCTTTAGCACTGAACATTCACCAAGTTCTATGCTTTTATGTAATCTCA 780 |
| | | ************************************************************ |
| Nipponbare | 781: | AATTTAACATTGTGTTTCCTTCACTCACCCTAGAATATACTACCTGAAAGCAATCAATG 840 |
| Kasalath | 781: | ATTTTAACATTGTGTTTTCCTTCACTCACCCTAGAATATACTACCTGAAAGCAATCAATG 840 |
| | | * *********************************************************** |
| Nipponbare | 841: | AAATCAAATATAACTTCGTTTCTACCTATATGATTGTAACATGCTGAGTAATATGGTGCC 900 |
| Kasalath | 841: | AAATCAAATATAACTTCGTTTCTACCTATATGATTGTAACATGCTGAGTAATATGGTGCC 900 |
| | | ************************************************************ |
| Nipponbare | 901: | AAACAACTCAACACATATAATACTGTCCTTAACAACCCATCTTCTTTTCCCTGTAGAAGT 960 |
| Kasalath | 901: | AAACAACTCAACACATATAATACTGTCCTTAACAACCCATCTTCTTTTCCCTGTAGAAGT 960 |
| | | ************************************************************ |
| Nipponbare | 961: | TACAGCCCTAGTATATTCTGTACATGTCATGCTACCTAGATGACAGTTGAGGCCTGGTAG 1020 |
| Kasalath | 961: | TGCAGCCCTAGTATATTCTGTACATGTCATGCTACCTAGATGACAATTGAGGCCTGGTAG 1020 |
| | | * ***************************************** ************** |
| Nipponbare | 1021: | GAGTGTGCTTGTTTAATTTTGGTACTCCAAAAGTGCACTGTTTTTCTCAATCTGACTCTG 1080 |
| Kasalath | 1021: | GAGTGTGCTTGTTTAATTTTGGTACTCCAAAAGTGCACTGTTTTTCTCAATCTGACTCTG 1080 |
| | | ************************************************************ |
| Nipponbare | 1081: | TTACCAGTTGTGTTTCCTCTAGATGTATTCCTTATCTATGGTGAATTATTAAATAAGTTG 1140 |
| Kasalath | 1081: | TTACCAGTTGTGTTTCCTCTAGATGTATTCCTTATCTATGGTGAATTATTAAATAAGTTG 1140 |
| | | ************************************************************ |
| Nipponbare | 1141: | TCTGGTGACAAAAA--AAAAAGAAAAATAAAAGAAGAGATGAACAATATGTAGCTCATTG 1198 |
| Kasalath | 1141: | TCTGGTGACAAAAAAGAAAAAGAAAAAGAAAAGAAGAGATGAACAATATGTAGCTCATTG 1200 |
| | | ************** ******** ************************************ |
| Nipponbare | 1199: | ATGATCCCTTGTCTGCTTGAACTTTATGAGAAACTATAGAAAGCAGTGGTGTTTTCCCTG 1258 |
| Kasalath | 1201: | ATGATCCCTTGTCTGCTTGAACTTTATGAGAAACTATAGAAAGCAGTGGTGTTTTCCCTG 1260 |
| | | ************************************************************ |
| Nipponbare | 1259: | ACCTGATGTTAAATACTTGTTAAGAATTGAGCTTTCTTCGAAGTTTGTTCAGTTTACACA 1318 |
| Kasalath | 1261: | ACCTGATGTTAAATACTTGTTAAGAATTGAGCTTTCTTCGAAGTTTGTTCAGTTTACACA 1320 |
| | | ************************************************************ |
| Nipponbare | 1319: | CCAACACTAAGAATTGCCATATATCTCCCATCTTTTGTCCATTTAATTCTTGTTACCTCA 1378 |
| Kasalath | 1321: | CCAACACTAAGAATTGCCATATATCT-CCATCTTTTGTCCATTTAATTCTTGTTACCTCA 1379 |
| | | ************************** ********************************* |
| Nipponbare | 1379: | AGTCATTGAGGGACCTGGCAGCATGTTATGACTTACACAATACCTCGCTAACTATTATGG 1438 |
| Kasalath | 1380: | AGTCATTGAGGGACCTGGCAGCATGTTATGACTTACACAATACCTCGCTAACTATTATGG 1439 |
| | | ************************************************************ |
| Nipponbare | 1439: | TGCATCTTTAACAGTGAGCAGGATGACTATGAAGTTGTCAGGAAAGTTGGAAGAGGTAAA 1498 |
| Kasalath | 1440: | TGCATCTTTAACAGTGAGCAGGATGACTATGAAGTTGTCAGGAAAGTTGGAAGAGGTAAA 1499 |
| | | ************************************************************ |
| | | Second exon |
| Nipponbare | 1499: | TATAGTGAAGTCTTTGAAGGCATCAATGTTAACAACAATGAGAAATGCATCATCAAGATA 1558 |
| Kasalath | 1500: | TATAGTGAAGTCTTTGAAGGCATCAATGTTAACAACAATGAGAAATGCATCATCAAGATA 1559 |
| | | ************************************************************ |

*FIG. 4C*

```
Nipponbare  1559:CTCAAGCCTGTGAAGAAAAAGAAGGTATTTAATTGATCTTATTGACTGTTTTTTTTAATT 1618
Kasalath    1560:CTCAAGCCTGTGAAGAAAAAGAAGGTATTTAATTGATCTTATTGACTGTTTTTTTTAATT 1619
                 ************************************************************
                                                                    Second intron
Nipponbare  1619:GCTAGTGTTGAAGTTCTTAACCTACCTTTCATATGTTTGAACAGATCAAAAGGGAGATTA 1678
Kasalath    1620:GCTAGTGTTGAAGTTCTTAACCTACCTTTCATATGTTTGAACAGATCAAAAGGGAGATTA 1679
                 ************************************************************
                                                                     Third exon
Nipponbare  1679:AAATACTTCAGAATCTTTGTGGAGGTCCAAACATTGTGTAGCTTCTTGATATTGTCAGAG 1738
Kasalath    1680:AAATACTTCAGAATCTTTGTGGAGGTCCAAACATTGTGAAGCTTCTTGATATTGTCAGAG 1739
                 ************************************** *********************
Nipponbare  1739:ATCAACATTCTAAGACTCCTAGCTTGATCTTTGAATATGTCAACAATACAGACTTCAAAG 1798
Kasalath    1740:ATCAACATTCTAAGACTCCTAGCTTGATCTTTGAATATGTCAACAATACAGACTTCAAAG 1799
                 ************************************************************
Nipponbare  1799:TGCTGTACCCCACGTTGACAGATTATGATATCCGCTACTACATATATGAGCTACTCAAGG 1858
Kasalath    1800:TGCTGTACCCCACGTTGACAGATTATGATATCCGCTACTACATATATGAGCTACTCAAGG 1859
                 ************************************************************
Nipponbare  1859:TCTTCATTGAGCCTTCATTGTCATCCCTATTTATTTACTCTATTCAGTAAAACATCCTGT 1918
Kasalath    1860:TCTTCATTGAGCCTTCATTGTCATCCCTATTTATTTACTCTATTCAGTAAAACATCCTGT 1919
                 ************************************************************
                 Third intron
Nipponbare  1919:TCTGTGGATCTGTAGAATGATGTATCTCTTATAGAAATTGTTTTCACAATTACTTTCCTA 1978
Kasalath    1920:TCTGTGGATCTGTAGAATGATGTATCTCTTATAGAAATTG-TTTCACAATTACTTTCCTA 1978
                 **************************************** *******************
Nipponbare  1979:TTATGTGAAGATCCAACTAAACACACTTGTAATATATCCTAGACAAATATCACCATTCTC 2038
Kasalath    1979:TTATGTGAAGATCCAACTAAACACACTTGTAATATATCCTAGACAAATATCACCATTCTC 2038
                 ************************************************************
Nipponbare  2039:ACTGCTTGCAAGTTGCAACATATCTTTAATTATTTATGTATATATGAACTTGATTATTTT 2098
Kasalath    2039:ACTGCTTGCAAGTTGCAACATATCTTTAATTATTTATGTATGTATGAACTTGATTATTTT 2098
                 ***************************************** ******************
Nipponbare  2099:CTAAAGTTACATGGCTTAAAACTTGTCACAATCTCAAGCAGTTTATGGATCAGTTTTGTT 2158
Kasalath    2099:CT-AAGTTACATGGCTTAAAACTTGTCACAATCTCAAGCAGTTTATGGATCAGTTTTGTT 2157
                 ** *********************************************************
Nipponbare  2159:TTGAGTTTTAATTATAGTAGCATCTTGCACTTCATAATGTACAGATGACAAAAGAATTCC 2218
Kasalath    2158:TTGAGTTTTAATTATAGTAGCATCTTGCACTTCATAATGTACAGATGACAAAAGAATTCC 2217
                 ************************************************************
Nipponbare  2219:TGAATTGCATATGTGCTATAATGGTTTATGATCTGGGATTTTGAAGAGAAGTGTCGTTTT 2278
Kasalath    2218:TGAATTGCATATGTGCTATAATGGTTTATGATCTGGGATTTTGAAGAGAAGTGTCGTTTT 2277
                 ************************************************************
Nipponbare  2279:ATACATTTCTAAGTTCAGCACTATGTTGGTGTTAAGAATTCAGCCATCAATGGGCATCTT 2338
Kasalath    2278:ATACATTTCTAAGTTCAGCACTATGTTGGTGTTAAGAATTCAGCCATCAATGGGCATCTT 2337
                 ************************************************************
Nipponbare  2339:AACGTATGTGCTAGGTCATGCCTTCTATCCATGGGTAATAAACTGTTAACACACAGTGTG 2398
Kasalath    2338:AACGTATGTGCTAGGTCATGCCTTCTATCCATGGGTAATAAACTGTTAACACACAGTGTG 2397
                 ************************************************************
Nipponbare  2399:TGTTTTTCATATCGATATTCTTAGCCAAGAACAGTAGCATCATTTGCCCTTAATCCTGTG 2458
Kasalath    2398:TGTTTTTCATATCGATATTCTTAGCCAAGAACAGTAGCATCATTTGCCCTTAATCCTGTG 2457
```

FIG. 4D

```
                   ************************************************************
Nipponbare  2459:TGTTAAGTTTGTTTAAAGAATCTAGTTGATTTTCTTTACAATATTTTCCTTCTGTTTATG 2518
Kasalath    2458:TGTTAAGTTTGTTTAACGAATCTAGTTGATTTTCTTTACAATATTTTCCTTCTGTTTATG 2517
                   *******************  ***************************************

Nipponbare  2519:GCCCCAGGCATTAGACTACTGCCATTCACAAGGCATTATGCATCGAGATGTCAAGCCCCA 2578
Kasalath    2518:GCCCCAGGCATTAGACTACTGCCATTCACAAGGCATTATGCATCGAGATGTCAAGCCCCA 2577
                   ************************************************************
                                           Fourth exon
Nipponbare  2579:CAATGTTATGATAGATCATGAGCTCCGAAAACTTCGATTGATAGACTGGGGCCTGGCTGA 2638
Kasalath    2578:CAATGTTATGATAGATCATGAGCTCCGAAAACTTCGATTGATAGACTGGGGCCTGGCTGA 2637
                   ************************************************************

Nipponbare  2639:GTTCTATCATCCAGGGAAGGAATATAATGTTCGTGTTGCTTCAAGGTTGGTGTAGTTACA 2698
Kasalath    2638:GTTCTATCATCCAGGGAAGGAATATAATGTTCGTGTTGCTTCAAGGTTGGTGTAGTTACA 2697
                   ************************************************************
                                                                    Fourth intron
Nipponbare  2699:AGCAAACTACTTGTTTGGTTATGATTTTCTTGCTTTTTTATTGAATTGGATTGCACCCTG 2758
Kasalath    2698:AGCAAACTACTTGTTTGGTTATGATTTTCTTGCTTTTTTATTGAATTGGATTGCACCCTG 2757
                   ************************************************************

Nipponbare  2759:ATAATCACTTGAATCATGAGAGGAAGCTAACTTAAGAAGGTAGCATCCCTGTTTTGCAGT 2818
Kasalath    2758:ATAATCACTTGAATCATGAGAGGAAGCTAACTTAAGAAGGTAGCATCCCTGTTTTGCAGT 2817
                   ************************************************************

Nipponbare  2819:TTGTTTGCTAACTTGGCTCTAGAAGCAATACGTGAACCGATAAATTACTTGGTTTGAATT 2878
Kasalath    2818:TTGTTTGCTAACTTGGCTCTAGAAGCAATACGTGAACCGATAAATTACTTGGTTTGAATT 2877
                   ************************************************************

Nipponbare  2879:CACTGCTACTGTTGAAGTCTGAATTGCCTAGTGGTCCTTTTGCAACATTAATGTTACGAA 2938
Kasalath    2878:CACTGCTACTGTTGAAGTCTGAATTGCCTAGTGGTCCTTTTGCAACATTAATGTTACGAA 2937
                   ************************************************************

Nipponbare  2939:ATGCTGAAAGTTAAGCAATGAAGCTGTTTACCCTTAAACAACTAAGTTTACGTCTGAAAA 2998
Kasalath    2938:ATGCTGAAAGTTAAGCAATGAAGCTGTTTACCCTTAAACAACTAAGTTTACGTCTGAAAA 2997
                   ************************************************************

Nipponbare  2999:AAAGGCAATAAAACAGATACCATTACTAGCCCTTTATTATTTTGTAAGCATGTTATCAC 3058
Kasalath    2998:AAAGGCAATAAAACAGATACCATTACTAGCCCTTTATTATTTTGTAAGCATGTTATCAC 3057
                   ************************************************************

Nipponbare  3059:TGGAGTATATCATGCAATTATTGGGTGTACGTCTGAAAAAAGGCAATAAAACAGATACCA 3118
Kasalath    3058:TGGAGTATATCATGCAATTATTGGGTGTACGTCTGAAAAAAGGCAATAAAACAGATACCA 3117
                   ************************************************************

Nipponbare  3119:TTACTAGGACTTTATTATTTTTGTAAGCATGTTATCACTGGAATAGATCATGCAATTATT 3178
Kasalath    3118:TTACTAGGACTTTATTATTTTTGTAAGCATGTTATCACTGGAACAGATCATGCAATTATT 3177
                   *******************************************  ***************

Nipponbare  3179:GCTTACTAATGCGTCAATTCTTTGCTCATTTTTGCTTTGGTACCTGAGTTGAGCATATGG 3238
Kasalath    3178:GCTTACTAATGCGTCAATTCTTTGCTCATTTTTGCTTTGGTACCTGAGTTGAGCATATGG 3237
                   ************************************************************

Nipponbare  3239:TTTCTCGTTTTTATTCAGGTATTTCAAGGGGCCTGAGCTTCTTGTTGATTTGCAAGATTA 3298
Kasalath    3238:TTTCTCGTTTTTATTCAGGTATTTCAAGGGGCCTGAGCTTCTTGTTGATTTGCAAGATTA 3297
                   ************************************************************
                                                                      Fifth exon
Nipponbare  3299:TGATTATTCTTTGGACATGTGGAGCCTTGGTTGCATGTTTGCTGGGATGGTATGTGTGGC 3358
Kasalath    3298:TGATTATTCTTTGGACATGTGGAGCCTTGGTTGCATGTTTGCTGGGATGGTATGTGTGGC 3357
```

*FIG. 4E*

```
                      ************************************************************
                                                                     Fifth intron
Nipponbare  3359:TGTAAAAAATATCGCCTGTCTAGGTCAATGTCTGGATATCTAATGTACTATTGTATTGAT 3418
Kasalath    3358:TGTAAAAAATATCGCCTGTCTAGGTCAATGTCTGGATATCTAATGTACTATTGTATTGAT 3417
                 ************************************************************

Nipponbare  3419:AATAAGTCTGACGTCTGAACTCAGTTAACTGTATGCTATGATGCAGATATTCCGCAAGGA 3478
Kasalath    3418:AATAAGTCTGACGTCTGAACTCAGTTAATTGTATGCTATGATGCAGATATTCCGCAAGGA 3477
                 ****************************  ******************************
                                                                     Sixth exon
Nipponbare  3479:GCCATTCTTCTATGGTCATGATAACCATGATCAACTTGTCAAGATCGCAAAGGTAAGTCC 3538
Kasalath    3478:GCCATTCTTCTATGGTCATGATAACCATGATCAACTTGTCAAGATCGCAAAGGTAAGTCC 3537
                 ************************************************************
                                                                     Sixth intron
Nipponbare  3539:CAGTTTGATTCTGGCCTCTCACATTTCTCAAGGGAAAAAAAA-TGGTTTGGTATGCCTGA 3597
Kasalath    3538:CAGTTTGATTCTGGCCTCTCACATTTCTCATGGGAAAAAAAATTGGTTTGGTATGCCTGA 3597
                 ******************************  *********  ****************

Nipponbare  3598:TAAAATGTTTAGTTATGCAACTCGTGTTTTGGACTGGTTGGTATACATGTTTTACTTTGT 3657
Kasalath    3598:TAAAATGTTTAGTTATGCAACTCGTGTTTTGGACTGGTTGGTATACATGTTTTACTTTGT 3657
                 ************************************************************

Nipponbare  3658:TTCTAAAAAAAATTGCTGTTTGTGCTCCTTTTAGCTTAGTACTCATATGTTATTCTGACA 3717
Kasalath    3658:TTCTAAAAAAAATTGCTGTTTGTGCTCCTTTTAGCTTAGTACTCATATGTTATTCTGACA 3717
                 ************************************************************

Nipponbare  3718:TATAAGCAGTGTGATGTCGTCAAAATAAATTATGTTCATTTGTAAATTGTGATTTTTGAA 3777
Kasalath    3718:TATAAGCAGTGTGATGTCGTCAAAATAAATTATGTTCATTTGTAAATTGTGATTTTTGAA 3777
                 ************************************************************

Nipponbare  3778:GTTCTTATTTGTTGCTCTCGAACTCTTACTAGGACGGTTATTGGCATTTAAAGATGTTTT 3837
Kasalath    3778:GTTCTTATTTGTTGCTCTCGAACTCTTACTAGGACGGTTATTGGCATTTAAAGATGTTTT 3837
                 ************************************************************

Nipponbare  3838:AAGCATCCAATAATGCCTCGAGTGTGTGTCAGCAGTGTTGATTCGCTTGTCATCAGTTGA 3897
Kasalath    3838:AAGCATCCAATAATGCCTCGAGTGTGTGTCAGCAGTGTTGATTCGCTTGTCATCAGTTGA 3897
                 ************************************************************

Nipponbare  3898:AAACTAAGTACTTTTCCAGCATTATGCTATTGATATCGGACTAAGGCAGATGTCATAATG 3957
Kasalath    3898:AAACTAAGTACTTTTCCAGCATTATGCTATTGATATCGGACTAAGGCAGATGTCATAATG 3957
                 ************************************************************

Nipponbare  3958:TACTTTGATATCTATGCAAATTTTATTCTTGATCTGTTTTAGTGGTTTATATAAGTGCTT 4017
Kasalath    3958:TACTTTGATATCTATGCAAATTTTATTCTTGATCTGTTTTAGTGGTTTATATAAGTGCTT 4017
                 ************************************************************

Nipponbare  4018:ATTTTGGAATAACAATAAAACAGCTATATGTGAAATATTGGTATCTGATCCATGTGTTTT 4077
Kasalath    4018:ATTTTGGAATAACAATAAAACAGCTATATGTGAAATATTGGTATCTGATCCATGTGTTTT 4077
                 ************************************************************

Nipponbare  4078:CCCCATCATTCTCAGGTACTTGGAACAGAAGCACTAAATGCTTATTTGAACAAGTACCAT 4137
Kasalath    4078:CCCCATCATTCTCAGGTACTTGGAACAGAAGCACTAAATGCTTATTTGAACAAGTACCAT 4137
                 ************************************************************
                                            Seventh exon
Nipponbare  4138:ATTGAGCTTGATCCTCAGCTTGAAGCTCTTGTTGGGAGGTACGTTGCCATGCTTTTAGAT 4197
Kasalath    4138:ATTGAGCTTGATCCTCAGCTTGAAGCTCTTGTTGGGAGGTACGTTGCCATGCTTTTAGAT 4197
                 ************************************************************
                                                                    Seventh intron
Nipponbare  4198:ATTGGTTTTGAACGGGAAGATTCAGAAGTATAACACTTACATATACATATGCAGGCATAG 4257
Kasalath    4198:ATTGGTTTTGAACGGGAAGATTCAGAAGTATAACACTTACATATACATATGCAGGCATAG 4257
```

*FIG. 4F*

```
                    ************************************************
                                                          Eighth exon
Nipponbare  4258:TAGAAAACCATGGTCGAAATTCATTAATGCTGATAACCAACATCTAGTATCTCCTGAGGT 4317
Kasalath    4258:TAGAAAACCATGGTCGAAATTCATTAATGCTGATAACCAACATCTAGTATCTCCTGAGGT 4317
                 ************************************************************

Nipponbare  4318:TTGTCAATGGCTCTTGCTGTTTCCAAATCAACCTTAAGATAATGTTTGCTTAACATCATG 4377
Kasalath    4318:TTGTCAATGGCTCTTGCTGTTTCCAAATCAACCTTAAGATAATGTTTGCTTAACATCATG 4377
                 ************************************************************
                 Eighth intron
Nipponbare  4378:CTTGTACATTTGTAGGCTGTAGATTTTCTTGATAAGCTTCTACGTTATGATCACCAAGAT 4437
Kasalath    4378:CTTGTACATTTGTAGGCTGTAGATTTTCTTGATAAGCTTCTACGTTATGATCACCAAGAT 4437
                 ************************************************************
                                 Ninth exon
Nipponbare  4438:AGGCTCACTGCACGTGAAGCTATGGTAAGTCTACCCCGACAGATAATATTTGTTACATTC 4497
Kasalath    4438:AGGCTCACTGCACGTGAAGCTATGGTAAGTCTACCCCGACAGATAATATTTGTTACATTC 4497
                                          ************************************************
                                         Ninth intron
Nipponbare  4498:CAAGAAGATACTGATTTTGTTTGACTGGATATTTCCTATTTATGTAACAGTATTGACTGT 4557
Kasalath    4498:CAAGAAGATACTGATTTTGTTTGACTGGATATTTCCTATTTATGTAACAGTATTGACTGT 4557
                 ************************************************************

Nipponbare  4558:TCACTGAGATTGTTAGTTTATTGCTGAATATTTTAGTATATATCCTCCTTTTTAGTCATA 4617
Kasalath    4558:TCACTGAGATTGTTAGTTTATTGCTGAATATTTTAGTATATATCCTCCTTTTTAGTCATA 4617
                 ************************************************************

Nipponbare  4618:AGAATTACATCAATGATGTCATAATAGTACTTTCATCTTCCTATCCTATCACACCTCTGT 4677
Kasalath    4618:AGAATTACATCAATGATGTCATAATAGTACTTTCATCTTCCTATCCTATCACACCTCTGT 4677
                 ************************************************************

Nipponbare  4678:TCAATTTTTATTTTAGGCATATTCTGTTTCACTTATTGCTCTGTATTATGACAATATCAT 4737
Kasalath    4678:TCAATTTTTATTTTAGGCATATTCTGTTTCACTTATTGCTCTGTATTATGACAATATCAT 4737
                 ************************************************************

Nipponbare  4738:AAAACATTTTCCTGACCCTCAACCAAAAATAGTTGGCAAGTTATGCATTTGTATAGGTAC 4797
Kasalath    4738:AAAACATTTTCCTGACCCTCAACCAAAAATAGTTGGCAAGTTATGCATTTGTATAGGTAC 4797
                 ************************************************************

Nipponbare  4798:ACTTCAACTAGGGATGCAAGTGGAGCGGGCAATCGGTTATTTTTTGCCTGTTTATCTCAA 4857
Kasalath    4798:ACTTCAACTAGGGATGCAAGTGGAGCGGGCAATCGGTTATTTTTTGCCCGTTTATCTCAA 4857
                 ************************************************ ***********

Nipponbare  4858:TTCTAGTTCAATTGTTGTAGGTATTTATGCAGGTAACAGGATTGCTTACTCGCATCGCTA 4917
Kasalath    4858:TTCTAGTTCAATTGTTGTAGGTATTTATGCAGGTAACGGGATTGCTCACTCGCATCGCTA 4917
                 ************************************* ******* **************

Nipponbare  4918:ACTTCAACCCAATATAATTTGGCAAATGGTGCATTTGGCAATAGATAGAAACCCTTCAAA 4977
Kasalath    4918:ACTTCAACCCAATATAATTTGGCAAATGGTGCATTTGGCAATAGATAGAAACCCTTCAAA 4977
                 ************************************************************

Nipponbare  4978:TTTCTCTGCCACATTGGCTTTTGTATGCAATGAACAACGTTTCATCTTCACATAGTATCT 5037
Kasalath    4978:TTTCTCTGCCACATTGGCTTTTGTATGCAATGAACAACGTTTCATCTTCACATAGTATCT 5037
                 ************************************************************

Nipponbare  5038:GGCCAGTTGTAGGAGGAACAAATTGTTATTTGATTACTCTTGGACTTCTCAAATTAATGC 5097
Kasalath    5038:GGCCAGTTGTAGGAGGAACAAATTGTTATTTGATTACTCTTGGACTTCTCAAATTAATGC 5097
                 ************************************************************

Nipponbare  5098:CATAATCATGAATACTTGCAGGCACATCCGTACTTCCTCCAAGTGAGAGCTGCAGAAAAT 5157
Kasalath    5098:CATAATCATGAATACTTGCAGGCACATCCGTACTTCCTCCAAGTGAGAGCTGCAGAAAAT 5157
```

*FIG. 4G*

```
                    ************************************************
                                       Tenth exon
Nipponbare  5158:AGCAGAGCACGACCACAATGATCTTGTGTACCTGCTAAAATGATGATCCAGCTGATGATC 5217
Kasalath    5158:AGCAGAGCACGACCACAATGATCTTGTGTACCTGCTAAAATGATGATCCAGCTGATGATC 5217
                    ************************************************
                                       Stop codon
Nipponbare  5218:CACGACGGTACTACTTTGAGTTTGTGTGAACGATCGTGGAATGTGCTTGTAGCCTTGCAT 5277
Kasalath    5218:CACGACGGTACTACTTTGAGTTTGTGTGAACGATCGTGGAATGTGCTTGTAGCCTTGTAT 5277
                 ********************************************************  **

Nipponbare  5278:TTGTAAACTGTAATTCACTCCGTTGGTTGCGTTTGATGAATGCCGTGACATGCACATAAT 5337
Kasalath    5278:TTGTAAACTGTAATTCACTCCGTTGGTTGCGTTTGATGAATGCCGTGACATGCACATAAT 5337
                 ************************************************************

Nipponbare  5338:TATTTATTTCTGTAATGTTTTACCATAACAACGATTAAGATGCAACAGGTACCTGTATGA 5397
Kasalath    5338:TATTTATTTCTGTAATGTTTTACCATAACAACGATTAAGATGCAACAGGTACCTGTATGA 5397
                 ************************************************************

Nipponbare  5398:CAGCATGAGCCTTGTTAAGCTTGTTTCGAAATGAGGCCGAAGTGCATGTCTTAGCTCGGT 5457
Kasalath    5398:CTGCATGAGCCTTGTTAAGCTTGTTTCGAAATGAGGCCGAAGTGCATGTCTTAGCTCGGT 5457
                 * **********************************************************

Nipponbare  5458:TCAAATTACTAAAATTAACTCTAGTAGTAAATATTGGGGCCAAAATTTGGCTGCTTATTT 5517
Kasalath    5458:TCAAATTACTAAAATTAACTCTAGTAGTAAATATTGGGGCCAAAATTTGGCTGCTTATTT 5517
                 ************************************************************

Nipponbare  5518:CACCACTAACTTATTTGGACCTTTAACGGGCCATTAAATATACAAACCGACCATTCATGG 5577
Kasalath    5518:CTCCACTAACTTATTTGGACCTTTAACGGGCCATTAAATATACAAACCGACCATTCATGG 5577
                 * **********************************************************

Nipponbare  5578:CACAGGTAGGCCTCAAATGGGCCCATAAATAGGCCTACCATGAGATATAATCAGGCCTTA 5637
Kasalath    5578:CACAGGTAGGCCTCAAATGGGCCCATAAATAGGCCTACCATGAGATATAATCAGGCCTTA 5637
                 ************************************************************

Nipponbare  5638:CATGGGCCATCGGTTGGATAAGCGGGGCCTAAATGGACCAAACCATGGATTCTCGGGGCG 5697
Kasalath    5638:CATGGGCCATCGGTTGGATAAGCGGGGCCTAAATGGACCAAACCATGGATTCTCGGGGCG 5697
                 ************************************************************

Nipponbare  5698:TAAATGCAGCATCCAAAATTGGGCGGTGAAGGTACCGTGTTCTCTCTCCCTGTTCTTTTA 5757
Kasalath    5698:TAAATGCAGCATCCAAAATTGGGCGGTGAAGGTACCGTGTTCTCTCTCCCTGTTCTTTTA 5757
                 ************************************************************

Nipponbare  5758:AGGGTTGAACCGTGTTATAACTCACAGAAGGAAAAATATCACGAAATATTTCGTCCTCAT 5817
Kasalath    5758:AGGGTTGAACCGTGTTATAACTCACAGAAGGAAAAATATCACGAAATATTTCGTCCTCAT 5817
                 ************************************************************

Nipponbare  5818:GTTATGTCACAAATTC                                             5833
Kasalath    5818:GTTATGTCACAAATTC                                             5833
                 ****************
```

*FIG. 4H*

```
rice         1:   MSKARVYADVNVLRPKEYWDYEALTVQWGEQDDYEVVRKVGRGKYSEVFEGINVN  55
Maize        1:   MSKARVYADVNVLRPKEYWDYEALTVQWGEQDDYEVVRKVGRGKYSEVFEGINVN  55
Arabidopsis  1:   MSKARVYTDVNVIRPKDYWDYESLNVQWGEQDDYEVVRKVGRGKYSEVFEGINMN  55
human        1:MSGPVPSRARVYTDVNTHRPREYWDYESHVVEWGNQDDYQLVRKLGRGKYSEVFEAINIT  60
fly          1:MT--LPSAARVYTDVNAHKPDEYWDYENYVVDWGNQDDYQLVRKLGRGKYSEVFEAINIT  58
nematode     1:MP-PIPSRARVYAEVNPSRPREYWDYEAHMIEWGQIDDYQLVRKLGRGKYSEVFEGFKMS  59
                                                                       I rice         56:NNEKCIIKILKPVKKKKIKREIKILQNLCGGPNIVKLLDIVRDQHSKTPSLIFEYVNNTD  115
Maize        56:NNEKCIIKILKPVKKKKIKREIKILQNLCGGPNIVKLLDIVRDQHSKTPSLIFEYVNNTD  115
Arabidopsis  56:NNEKCIIKILKPVKKKEIRREIKILQNLCGGPNIVKLLDVVRDQHSKTPSLIFEYVNSTD  115
human        61:NNEKVVVKILKPVKKKKIKREIKILENLRGGPNIITLADIVKDPVSRTPALVFEHVNNTD  120
fly          59:TTEKCVVKILKPVKKKKIKREIKILENLRGGTNIITLLAVVKDPVSRTPALIFEHVNNTD  118
nematode     60:TDEKVVVKILKPVKKKKIKREIKILENLRGGTNIITLLDVVKDPISRTPALIFEHVNNSD  119
                          II                III      IV           V
             (nucleotide binding)

rice         116:FKVLYPTLTDYDIRYYIYELLKALDYCHSQGIMHRDVKPHNVMIDHELRKLRLIDWGLAE  175
Maize        116:FKVLYPTLTDYDIRYYIYELLKALDYCHSQGIMHRDVKPHNVMIDHELRKLRLIDWGLAE  175
Arabidopsis  116:FKVLYPTLTDYDIRYYIYELLKALDFCHSQGIMHRDVKPHNVMIDHGLRKLRLIDWGLAE  175
human        121:FKQLYQTLTDYDIRFYMYEILKALDYCHSMGIMHRDVKPHNVMIDHEHRKLRLIDWGLAE  180
fly          119:FKQLYQTLTDYEIRYYLFELLKALDYCHSMGIMHRDVKPHNVMIDHENRKLRLIDWGLAE  178
nematode     120:FKQLYQTLSDYDIRYYLYELLKALDFCHSQGIMHRDVKPHNVMIDAEKRELRLIDWGLAE  179
                                IV                                  VII
                                                        (nucleotide binding)

rice         176:FYHPGKEYNVRVASRYFKGPELLVDLQDYDYSLDMWSLGCMFAGMIFRKEPFFYGHDNHD  235
Maize        176:FYHPGKEYNVRVASRYFKGPELLVDLQDYDYSLDMWSLGCMFAGMIFRKEPFFYGHDNHD  235
Arabidopsis  176:FYHPGKEYNVRVASRYFKGPELLVDLQDYDYSLDMWSLGCMFAGMIFRKEPFFYGHDNQD  235
human        181:FYHPGQEYNVRVASRYFKGPELLVDYQMYDYSLDMWSLGCMLASMIFRKEPFFHGHDNYD  240
fly          179:FYHPGQEYNVRVASRYFKGPELLVDYQMYDYSLDMWSLGCMLASMIFRKEPFFHGHDNYD  238
nematode     180:FYHPRQDYNVRVASRYFKGPELLVDYQCYDYSLDMWSLGCMLASMIFRKEPFFHGHDNYD  239
                     VIII                              IX rice         236:QLVKIAKVLGTEALNAYLNKYHIELDPQLEALVGRHSRKPWSKFINADNQHLVSPEAVDF  295
Maize        236:QLVKIAKVLGTDGLNVYLNKYRIELDPQLEALVGRHSRKPWLKFMNADNQHLVSPEAIDF  295
Arabidopsis  236:QLVKIAKVLGTDELNAYLNKYQLELDTQLEALVGRHSRKPWSKFINADNRHLVSPEAIDY  295
human        241:QLVRIAKVLGTEDLYDYIDKYNIELDPRFNDILGRHSRKRWERFVHSENQHLVSPEALDF  300
fly          239:QLVRIAKVLGTEELYAYLDKYNIDLDPRFHDILQRHSRKRWERFVHSDNQHLVSPEALDF  298
nematode     240:QLVRIAKVLGTDELYEYIARYHIDLDPRFNDILGRHSRKRWERFIHAENQHLVTPEALDF  299
                                                X rice         296:LDKLLRYDHQDRLTAREAMAHPYF-LQVRAAENSRARPQ                       333
Maize        296:LDKLLRYDHQERLTALEAMTHPYF-QQVRAAENSRTRA                        332
Arabidopsis  296:LDKLLRYDHQDRLTAKEAMAHPYF-AQVRAAESSRMRTQ                       333
human        301:LDKLLRYDHQSRLTAREAMEHPYFYTVVKDQARMGSSSMPGGSTPVSSANMMSGISSVPT  360
fly          299:LDKLLRYDHVDRLTAREAMAHPYFLPIVNGQ--MNPNNQQ                      336
nematode     300:LDKLLRYDHAERLTAQEAMGHEYFRPVVEAHARANGTEQADGQGASNSASSQSSDAKIDG  359
                                         XI rice         334:
Maize        333:
Arabidopsis  334:
human        361:PSPLGPLAGSPVIAAANPLGMPVPAAAGAQQ                               391
fly          337:
nematode     360:A                                                             360
```

*FIG. 5*

PHOTOSENSITIVITY GENE OF PLANT AND UTILIZATION THEREOF

TECHNICAL FIELD

The present invention relates to genes involved in plant photoperiod sensitivity, and methods for modifying photoperiod sensitivity in plants using the genes. Methods to modify plant photoperiod sensitivity are useful for breeding plants.

BACKGROUND ART

Generally, heading (flowering) of rice is accelerated by short-day and delayed by long-day conditions. Among known cultivars, typically those from Kyushu and the south of Mainland Japan have strong photoperiod sensitivity whereas cultivars from the Tohoku district or Hokkaido show complete loss of such sensitivity or have extremely weak photoperiod sensitivity. Rice plants that lack the photoperiod sensitivity have a characteristic to flower after a certain length of growth period, and the heading date of the plant does not change with changes of photoperiod. Adaptation of rice plants related to cultivation locations and season drastically changes in accordance with the existence of photoperiod sensitivity in the plant. Thus, modification of photoperiod sensitivity in rice is an important aspect of breeding rice.

In conventional breeding programs, the alteration of the heading date of rice is achieved through methods involving: (1) selection of early maturing varieties or late varieties by crossing; and (2) mutagenesis by radiation and chemicals; and so on. However, such breeding programs require long periods of time to be successful, and bear other problems, such as unpredictability of the degree or direction of the mutations in the progeny.

"Photoperiod sensitivity gene" is a generic name for genes that enhance the rice photoperiod sensitivity in the field of rice genetics. The existence of several photoperiod sensitivity genes has been observed to be inherent in mutants and cultivars, and photoperiod sensitivity genes are suggested to exist on loci, for example, such as Se1 locus (chromosome 6; Yokoo and Fujimaki (1971) Japan. J. Breed. 21: 35–39), E1 locus (chromosome 7; Tsai, K. H. (1976) Jpn. J. Genet. 51: 115–128; Okumoto, Y. et al. (1992) Jpn. J. Breed. 42: 415–429), E2 locus (unknown), E3 locus (chromosome 3?; Okumoto et al. Japanese Society of Breeding, 91st lecture, Japanese Journal of Breeding 47 (Suppl. 1): 31); and so on (Yamagata et al. (1986) In Rice Genetics, International Rice Research Institute, Manilla, pp351–359).

Isolation of rice photoperiod sensitivity genes enables the introduction of such genes into arbitrary cultivars by transformation methods to modify the photoperiod sensitivity in these cultivar lines, which ultimately permits regulation of the heading date of the rice. Therefore, breeding using such genes is a particularly efficient yet simple and reliable method as compared to conventional methods.

However, the isolation of genes involved in the photoperiod sensitivity of rice has not yet been reported.

DISCLOSURE OF THE INVENTION

This need in the art led to the present invention, and the object of the present invention is to provide novel plant photoperiod sensitivity genes, specifically genes derived from rice. Another object of the present invention is to modify plant photoperiod sensitivity using such genes to modify the flowering time of the plant. Furthermore, another object of the present invention is to provide methods for assessing plant photoperiod sensitivity.

The present inventors focused specifically on rice, for which a simple method to modify the heading date was desired, and vigorously carried out studies to isolate genes related to rice photoperiod sensitivity.

A quantitative trait locus of rice, Hd6, identified using a progeny derived from a cross between Nipponbare and Kasalath, is known to exist on chromosome 3. Additionally, according to analyses on the Hd6 region with a genetic background of Nipponbare using nearly isogenic lines (Yamamoto et al. (1996) Abstract for Plant Genome IV. p124), the Hd6 gene locus has been revealed to be the locus of photoperiod sensitivity genes.

The present inventors first aligned the Hd6 gene region by linkage analysis using yeast artificial chromosome (YAC) clones to isolate the photoperiod sensitivity gene Hd6, a gene whose existence was known but which had not yet been isolated.

Specifically, the present inventors conducted linkage analysis of a large segregating population (200+980=1180 plants), which analysis is essential for the isolation of the Hd6 gene. A CAPS marker was used in the analysis to improve the efficiency of performance. Furthermore, a fine-scale physical map of the YAC clones around the candidate region of the Hd6 gene was constructed based of the contig map of YAC clones constructed in the Rice Genome Research Program. The Hd6 gene region was delimited to a region between markers E11893 and Y3626L using DNA end-fragments of YAC clone and cDNA clones on respective YAC clones as RFLP markers.

Next, the present inventors aligned the Hd6 gene regions using P1 derived artificial chromosome (PAC) clones. More specifically, DNA clones around the Hd6 gene region determined by the above analysis were used to select, from the genomic library of Nipponbare, 7 PAC clones purportedly comprising the nucleotide sequence of the DNA clones. Further, the alignment state of these clones was investigated to reveal that the PAC clone P0689D1 contained the candidate region of the Hd6 gene (FIG. 1).

The present inventors successfully mapped the region wherein the Hd6 candidate gene was presumed to exist to a site of about 26.4 kb by analyzing the nucleotide sequence of the PAC clone P0689D1. Gene prediction analysis and similarity search was conducted against the nucleotide sequence of the candidate region to find a region showing high similarity with the *Arabidopsis* CKIIα gene (FIGS. 2 and 3). The CKIIα gene is reported to be involved in the activation of the CCA1 (circadian clock) gene in *Arabidopsis*.

The nucleotide sequence of the Kasalath genomic CKIIα gene was determined using the nucleotide sequence information of the Nipponbare CKIIα gene. Then, the two sequences were compared to each other. As a result, a termination codon was identified in the protein-coding region of the Nipponbare CKIIα gene, but not in that of Kasalath (FIGS. 4A–4H). The expression of the candidate gene CKIIα in Nipponbare, which is suggested to lack the photoperiod sensitivity gene Hd6, and in nearly isogenic lines of Nipponbare having the Hd6 gene of Kasalath was compared using the RT-PCR method to reveal that the transcription level of the Hd6 candidate gene, the CKIIα gene, is markedly low in Nipponbare as compared to Hd6 nearly isogenic lines (FIG. 7). From the above, the inventors concluded that the Kasalath CKIIα gene was the rice photoperiod sensitivity gene Hd6.

Thus, the use of the Hd6 gene and other plant genes having the same function as the Hd6 gene has been enabled by the isolation of the Hd6 gene, which confers photoperiod sensitivity to rice plants. The use of such genes allows for the modification of the heading date of rice, and further, for the modification of the flowering time in a wide variety of plants. Moreover, this allows for breeding plant cultivars with modified adaptability to cultivation locations and seasons.

Further, the present inventors revealed that a specific restriction enzyme Hind III recognition site in Kasalath is generated through a difference of a nucleotide between the ORF of Nipponbare Hd6 gene and that of Kasalath Hd6 gene. The use of the different nucleotide in determining the existence or absence of the photoperiod sensitivity genes in rice cultivars by a restriction enzyme fragment polymorphism analysis has been indicated. On the other hand, the photoperiod sensitivity gene E3 was proposed to exist on chromosome 3 and its position was proposed to correspond to the position of Hd6. Accordingly, the present inventors examined the validity of this restriction enzyme fragment polymorphism analysis on cultivar population, wherein the existence or absence of the photoperiod sensitivity gene E3 therein has been already determined by a genetic analysis (Okumoto et al. (1991) International Rice Research Institute, Rice Genetics II pp. 778–780). As a result, the inventors found that the amplified fragments of the Hd6 gene in cultivars determined to lack E3 were not digested with Hind III whereas those of 8 cultivars determined to retain E3 were digested with the enzyme. Thus, it was revealed by the present inventors that the photoperiod sensitivity of rice cultivars could be efficiently determined by methods identifying the existence or absence of a termination codon at a specific site in the Hd6 gene.

In other words, the present inventors succeeded in isolating a gene involved in photoperiod sensitivity of plants. The present inventors also found that the photoperiod sensitivity of plants can be modified using the gene, and that the photoperiod sensitivity of plants can be assessed by the gene, and finally completed the present invention.

More specifically, this invention provides the following:

(1) a DNA encoding a protein derived from plants that increases the photoperiod sensitivity of plants, said DNA being selected from the group of:

(a) a DNA encoding the protein comprising the amino acid sequence of SEQ ID NO: 1;

(b) a DNA encoding the protein comprising the amino acid sequence of SEQ ID NO: 1, wherein one or more of the amino acids are substituted, deleted, added and/or inserted;

(c) a DNA hybridizing under stringent conditions with the DNA consisting of the nucleotide sequence of SEQ ID NO: 2;

(2) the DNA of (1), wherein the DNA is derived from rice;

(3) a DNA encoding an antisense RNA complementary to the transcription product of the DNA of any one of (1) and (2);

(4) a DNA encoding an RNA having the activity of a ribozyme that specifically digests the transcription product of the DNA of (1) or (2);

(5) a DNA encoding an RNA that represses the expression of the DNA of (1) or (2) upon expression in a plant cell due to a corepressing effect;

(6) a DNA of (1) or (2), wherein the DNA is used to increase the photoperiod sensitivity of plants;

(7) a DNA of any one of (3) to (5), which DNA is used to reduce the photoperiod sensitivity of plants;

(8) a vector comprising the DNA of any one of (1) to (5);

(9) a plant cell transformed with the vector of (8);

(10) a plant transformant comprising the plant cell of (9);

(11) the plant transformant of (10), wherein said plant transformant is rice;

(12) a plant transformant which is a progeny or a clone of the plant transformant of (10) or (11);

(13) a breeding material of the plant transformant of any one of (10) to (12);

(14) a method for producing the plant transformant of (10) or (11), which comprises the following steps of:

(a) introducing the DNA of (1) or (2) into a plant cell, and
(b) regenerating a plant from the plant cell;

(15) a method for increasing the photoperiod sensitivity of plants, said method comprising the step of expressing the DNA of (1) or (2) in cells of the plant body;

(16) the method of (15), wherein the flowering time of a plant dependent on the photoperiod is delayed by increasing the photoperiod sensitivity of the plant;

(17) a method for decreasing the photoperiod sensitivity of plants, said method comprising the step of repressing the expression of the DNA of (1) or (2) in cells of the plant body, wherein said DNA is endogenous to said plant cells;

(18) the method of (17), wherein the DNA of any one of (3) to (5) is expressed within the cells of the plant body;

(19) the method of (17) or (18), wherein the flowering of the plant dependent on the photoperiod is accelerated by the decrease in photoperiod sensitivity of the plant;

(20) a method of any one of (15) to (19), wherein the plant is rice;

(21) a method for assessing the photoperiod sensitivity of plants, comprising the step of detecting the presence or absence of the DNA of (1) in the plant;

(22) the method of (21), wherein the plant is rice;

(23) the method of (22), wherein substitution of the 2815th nucleotide, "A", in the nucleotide sequence of SEQ ID NO: 2 for the nucleotide "T" is detected;

(24) the method of (23), further comprising the steps of:

(a) conducting polymerase chain reaction using rice genomic DNA as the template and primer pairs against the DNA consisting of the nucleotide sequence of SEQ ID NO: 2 or the complementary strand thereof, wherein said primer pairs are designed to sandwich the 2815th nucleotide "An" of the nucleotide sequence of SEQ ID NO: 2;

(b) reacting the restriction enzyme Hind III with the DNA fragments amplified by the polymerase chain reaction in step (a); and (c) detecting whether the DNA fragments are digested by the action of the restriction enzyme Hind III;

(25) a host cell wherein a vector comprising the DNA of (1) or (2) has been inserted;

(26) a protein encoded by the DNA of (1) or (2);

(27) a method for producing the protein of (26) comprising the following steps of:

(a) culturing a host cell of (25), and (b) recovering the recombinant protein from the host cell or the culture supernatant thereof;

(28) an antibody binding to the protein of (26); and

(29) a DNA comprising at least 15 nucleotides that are complementary to a DNA consisting of the nucleotide sequence of SEQ ID NO: 2 or to a complementary strand thereof.

The present invention provides DNAs encoding the Hd6 protein derived from rice. The nucleotide sequences of the genomic DNA and cDNA of the Kasalath Hd6 isolated by the present inventors are shown in SEQ ID NO: 2 and 3, respectively. The amino acid sequence of the protein encoded by these DNAs is shown in SEQ ID NO: 1. Additionally, the nucleotide sequence of the Nipponbare Hd6 genomic DNA is shown in SEQ ID NO: 5, and the amino acid sequence of the protein encoded by the DNA is shown in SEQ ID NO: 4.

The Hd6 is one of quantitative trait loci (QTL) detected by using progeny lines of a cross between Nipponbare and Kasalath, and it was known to exist on chromosome 3. Additionally, it was known that the Hd6 locus was a photoperiod sensitivity gene locus according to an experiment using a nearly isogenic line on Hd6 region with a genetic background of Nipponbare. This nearly isogenic line needed about 5 to 7 days more for heading from seeding (heading date) as compared to that of Nipponbare. In other words, Hd6 can intensify the photoperiod sensitivity to delay heading. The Hd6 gene has been known to be a gene involved in photoperiod sensitivity of plants and to exist somewhere within the vast region of chromosome 3. However, the Hd6 gene had not been identified nor isolated. After performing complicated examination steps, the present inventors finally identified the region where the gene exists, and succeeded for the first time in isolating the gene as a single gene.

Today, it is an important object to control the heading date of rice in the breeding of rice in Japan. It is important to evade cold weather damage in cold districts due to the early coming of low-temperature of fall. On the other hand, to abridge the labor due to centralization of harvest time in the extensive rice-growing region in the west-south warm area, there is a need to accelerate or to delay the heading date.

The heading date of plants (flowering time) can be delayed by transforming plants with a DNA encoding the Hd6 protein which enhances the photoperiod sensitivity of plants. Alternatively, control of the expression of the DNA using the antisense method or the ribozyme method enables reduced photoperiod sensitivity, and accelerated flowering time of plants. Specifically, the flowering time of plants can be diversified by recombinantly introducing a DNA encoding the Hd6 protein to plants lacking the DNA and by controlling expression of the DNA in cultivars having the DNA using antisense, ribozymes, and such. Thus, new kinds of cultivars can be bred.

DNA encoding the Hd6 protein of the present invention includes genomic DNA, cDNA, and chemically synthesized DNA. A genomic DNA and cDNA can be prepared according to conventional methods known to those skilled in the art. More specifically, a genomic DNA can be prepared, for example, as follows: (1) extract genomic DNA from rice cultivars having the photoperiod sensitivity gene (e.g. Kasalath); (2) construct a genomic library (utilizing a vector, such as plasmid, phage, cosmid, BAC, and so on); (3) spread the library; and (4) conduct colony hybridization or plaque hybridization using a probe prepared based on the DNA encoding a protein of the present invention (e.g. SEQ ID NO: 2). Alternatively, a genomic DNA can be prepared by PCR, using primers specific to a DNA encoding the protein of s present invention (e.g. SEQ ID NO: 2). On the other hand, cDNA can be prepared, for example, as follows: (1) synthesize cDNAs based on mRNAs extracted from rice cultivars having the photoperiod sensitivity gene (e.g. Kasalath); (2) prepare a cDNA library by inserting the synthesized cDNA into vectors, such as λZAP; (3) spread the cDNA library; and (4) conduct colony hybridization or plaque hybridization as described above. Alternatively, cDNA can be also prepared by PCR.

The present invention includes DNAs encoding proteins functionally equivalent to the Hd6 protein of SEQ ID NO: 1. Herein, the term "functionally equivalent to the Hd6 protein" indicates that the object protein has the function of enhancing the photoperiod sensitivity of plants. Examples of such DNAs include those encoding mutants, derivatives, alleles, variants, and homologues comprising the amino acid sequence of SEQ ID NO: 1 wherein one or more amino acids are substituted, deleted, added and/or inserted.

Examples of methods for preparing a DNA encoding a protein comprising altered amino acids well known to those skilled in the art include the site-directed mutagenesis (Kramer, W. and Fritz, H.-J., "Oligonucleotide-directed construction of mutagenesis via gapped duplex DNA." Methods in Enzymology, 154: 350–367, 1987). The amino acid sequence of a protein may also be mutated in nature due to the mutation of a nucleotide sequence. A DNA encoding proteins having the amino acid sequence of a natural Hd6 protein wherein one or more amino acids are substituted, deleted, and/or added are also included in the DNA of the present invention, so long as they encode a protein functionally equivalent to the natural Hd6 protein (SEQ ID NO: 1). Additionally, nucleotide sequence mutants that do not give rise to amino acid sequence changes in the protein (degeneracy mutants) are also included in the DNA of the present invention.

Assessment of whether a DNA encodes a protein that enhances the photoperiod sensitivity of plants or not can be performed as follows: The most general method involves transforming with the DNA a plant and growing the plant in a growth cabinet wherein the length of day can be changed. More specifically, plants are grown under short-day condition (generally, 9 to 10 hours) or long-day condition (14 to 16 hours), and the number of days needed from seeding to flowering (when the plant is rice, from seeding to heading) is compared between plants grown under these different conditions. Plants that show no difference in the number of days-to-heading between the long-day and short-day conditions are determined to lack photoperiod sensitivity. Plants that show a difference in the number of days-to-heading between the two conditions are determined to have photoperiod sensitivity, and the difference is considered as the degree of photoperiod sensitivity of the plant. In those cases where a growth cabinet is not available, the assessment can be also performed by growing plants in fields and in greenhouses with natural day length. Specifically, plants are seeded every 20th day and are grown under natural day length under constant temperature to determine days needed for flowering in respective plants. Generally, the heading of rice cultivars with strong photoperiod sensitivity are accelerated when seeded during August to February, and those seeded between April to July are delayed. On the other hand, days-to-heading in rice cultivars having weak photoperiod sensitivity is not influenced by the season of seeding and doesn't change greatly according to day length.

A DNA encoding a protein functionally equivalent to the Hd6 protein described in SEQ ID NO: 1 can be produced, for example, by methods well known to those skilled in the art including: methods using hybridization techniques (Southern, E.M.: Journal of Molecular Biology, Vol. 98, 503, 1975.); and polymerase chain reaction (PCR) techniques (Saiki, R. K. et al. Science, vol. 230, 1350–1354, 1985; Saiki, R. K. et al. Science, vol. 239, 487–491, 1988). That is, it is routine for a person skilled in the art to isolate a DNA with high homology to the Hd6 gene from rice and other plants using the nucleotide sequence of the Hd6 gene (SEQ ID NO: 2 or 3) or parts thereof as a probe, and oligonucleotides hybridizing specifically to the nucleotide sequence of Hd6 gene (SEQ ID NO: 2 or 3) as a primer. Such DNA encoding proteins functionally equivalent to the Hd6 protein, obtainable by hybridization techniques or PCR techniques, are included in the DNA of this invention.

Hybridization reactions to isolate such DNAs are preferably conducted under stringent conditions. Stringent hybridization conditions of the present invention include conditions such as: 6M urea, 0.4% SDS, and 0.5×SSC; and those which yield a similar stringency with the conditions. DNAs with higher homology are expected when hybridization is performed under conditions with higher stringency, for example, 6M urea, 0.4% SDS, and 0.1×SSC. Those DNAs isolated under such conditions are expected to encode a protein having a high amino acid level homology with Hd6 protein (SEQ ID NO: 1). Herein, high homology means an identity of at least 50% or more, more preferably. 70% or more, and much more preferably 90% or more (e.g. 95% or more). The degree of homology of one amino acid sequence or nucleotide sequence to another can be determined by following the algorithm BLAST by Karlin and Altschl (Proc. Natl. Acad. Sci. USA, 90: 5873–5877, 1993). Programs such as BLASTN and BLASTX were developed based on this algorithm (Altschul et al. J. Mol. Biol. 215: 403–410, 1990). To analyze a nucleotide sequences according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST program. Specific techniques for such analysis are known in the art (http://www.ncbi.nlm.nih.gov.)

The DNA of the present invention can be used, for example, to prepare recombinant proteins, produce plant transformants with altered photoperiod sensitivity, and so on.

A recombinant protein is usually prepared by inserting a DNA encoding a protein of the present invention into an appropriate expression vector, introducing said vector into an appropriate cell, culturing the transformed cells, and purifying expressed proteins. A recombinant protein can be expressed as a fusion protein with other proteins so as to be easily purified, for example, as a fusion protein with maltose binding protein in *Escherichia coli* (New England Biolabs, USA, vector pMAL series), as a fusion protein with glutathione-S-transferase (GST) (Amersham Pharmacia Biotech, vector pGEX series), or tagged with histidine (Novagen, pET series). The host cell is not limited so long as the cell is suitable for expressing the recombinant protein. It is possible to utilize yeasts or various animal, plant, or insect cells besides the above described *E. coli*. A vector can be introduced into a host cell by a variety of methods known to one skilled in the art. For example, a transformation method using calcium ions (Mandel, M. and Higa, A., J. Mol. Biol. 53: 158–162, (1970); Hanahan, D., J. Mol. Biol. 166: 557–580, (1983)) can be used to introduce a vector into *E. coli*. A recombinant protein expressed in host cells can be purified and recovered from the host cells or the culture supernatant thereof by known methods. When a recombinant protein is expressed as a fusion protein with maltose binding protein or other partners, the recombinant protein can be easily purified by affinity chromatography.

The resulting protein can be used to prepare an antibody that binds to the protein. For example, a polyclonal antibody can be prepared by immunizing immune animals, such as rabbits, with a purified protein of the present invention or its portion, collecting blood after a certain period, and removing clots. A monoclonal antibody can be prepared by fusing myeloma cells with the antibody-forming cells of animals immunized with the above protein or its portion, isolating a monoclonal cell expressing a desired antibody (hybridoma), and recovering the antibody from the said cell. The obtained antibody can be utilized to purify or detect a protein of the present invention. Accordingly, the present invention includes antibodies that binds to proteins of the invention.

A plant transformant with increased photoperiod sensitivity can be created using DNAs of the present invention. More specifically, a DNA encoding a protein of the present invention is inserted into an appropriate vector; the vector is introduced into a plant cell; and then, the resulting transformed plant cell is regenerated. The photoperiod sensitivity gene Hd6, isolated by the present inventors, functions to enhance the photoperiod sensitivity of rice, and can delay the heading date of rice. Therefore, the heading date of arbitrary cultivars can be controlled by transforming the cultivars with the gene and expressing the same. The time needed for transformation is remarkably short as compared to ordinary gene transfer by crossing. Furthermore, the fact that the transformation doesn't accompany other characteristical changes is also beneficial. Genes controlling the heading date of rice are newly identified and isolated herein, and controlling of heading date of rice is enabled for the first time by the present invention.

On the other hand, a plant transformant with reduced photoperiod sensitivity can be created using DNA that represses the expression of a DNA encoding a protein of the present invention: wherein the DNA is inserted into an appropriate vector, the vector is introduced into a plant cell, and then, the resulting transformed plant cell is regenerated. The phrase "repression of expression of DNA encoding a protein of the present invention" includes repression of gene transcription as well as repression of translation into protein. It also includes not only the complete inability of expression of DNA but also reduction of expression.

The expression of a specific endogenous gene in plants can be repressed by methods utilizing antisense technology, which are commonly used in the art. Ecker et al. were the first to demonstrate the antisense effect of an antisense RNA introduced by electroporation in plant cells by using the transient gene expression method (J. R. Ecker and R. W. Davis, Proc. Natl. Acad. Sci. USA 83: 5372 (1986)). Thereafter, the target gene expression was reportedly reduced in tobacco and petunias by expressing antisense RNAs (A. R. van der Krol et al., Nature 333: 866 (1988)). The antisense technique has now been established as a means to repress target gene expression in plants. Multiple factors are required for antisense nucleic acid to repress the target gene expression. These include: inhibition of transcription initiation by triple strand formation; repression of transcription by hybrid formation at the site where the RNA polymerase has formed a local open loop structure; transcription inhibition by hybrid formation with the RNA being synthesized; repression of splicing by hybrid formation at the junction between an intron and an exon; repression of splicing by hybrid formation at the site of spliceosome formation; repression of mRNA translocation from the nucleus to the cytoplasm by hybrid formation with mRNA; repression of splicing by hybrid formation at the capping site or at the poly A addition site; repression of translation initiation by hybrid formation at the binding site for the translation initiation factors; repression of translation by hybrid formation at the site for ribosome binding near the initiation codon; inhibition of peptide chain elongation by hybrid formation in the translated region or at the polysome binding sites of mRNA; and repression of gene expression by hybrid formation at the sites of interaction between nucleic acids and proteins. These factors repress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)", Nihon Seikagakukai Hen (The Japanese Biochemical Society), Tokyo Kagaku Dozin, pp. 319–347, (1993)).

An antisense sequence of the present invention can repress the target gene expression by any of the above mechanisms. In one embodiment, if an antisense sequence is designed to be complementary to the untranslated region near the 5'end of the gene's mRNA, it will effectively inhibit translation of a gene. It is also possible to use sequences complementary to the coding regions or to the untranslated region on the 3' side. Thus, the antisense DNA used in the present invention include DNA having antisense sequences against both the untranslated regions and the translated regions of the gene. The antisense DNA to be used is connected downstream from an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene of the plant to be transformed or a part thereof, but it need not be perfectly complementary so long as it can effectively inhibit the gene expression. The transcribed RNA is preferably at least 90%, and most preferably at least 95% complementary to the transcribed products of the target gene. In order to effectively inhibit the expression of the target gene by means of an antisense sequence, the antisense DNA should be at least 15 nucleotides long, more preferably at least 100 nucleotides long, and still more preferably at least 500 nucleotides long. The antisense DNA to be used is generally shorter than 5 kb, and preferably shorter than 2.5 kb.

DNA encoding ribozymes can also be used to repress the expression of endogenous genes. A ribozyme is an RNA molecule that has catalytic activities. There are many ribozymes having various activities. Research on the ribozymes as RNA cleaving enzymes has enabled the design of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka, Tanpakushitsu Kakusan Kohso (Nucleic acid, Protein, and Enzyme), 35: 2191 (1990)).

The self-cleavage domain of a hammerhead type ribozyme cleaves at the 3' side of C15 of the sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (M. Koizumi et al., FEBS Lett. 228: 225 (1988)). If the substrate binding site of the ribozyme is designed to be complementary to the RNA sequences adjacent to the target site, one can create a restriction-enzyme-like RNA cleaving ribozyme which recognizes the sequence UC, UU, or UA within the target RNA (M. Koizumi et al., FEBS Lett. 239: 285 (1988); Makoto Koizumi and Eiko Ohtsuka, Tanpakushitsu Kakusan Kohso (Protein, Nucleic acid, and Enzyme), 35: 2191 (1990); M. Koizumi et al., Nucleic Acids Res. 17: 7059 (1989)). For example, in the coding region of the Hd6 gene (SEQ ID NO: 3), there are a plurality of sites that can be used as the ribozyme target.

The hairpin type ribozyme is also useful in the present invention. A hairpin type ribozyme can be found, for example, in the minus strand of the satellite RNA of tobacco ringspot virus (J. M. Buzayan, Nature 323: 349 (1986)). This ribozyme has also been shown to target-specifically cleave RNA (Y. Kikuchi and N. Sasaki, Nucleic Acids Res. 19: 6751 (1992); Yo Kikuchi, Kagaku To Seibutsu (Chemistry and Biology) 30: 112 (1992)).

The ribozyme designed to cleave the target is fused with a promoter, such as the cauliflower mosaic virus 35S promoter, and with a transcription termination sequence, so that it will be transcribed in plant cells. However, if extra sequences have been added to the 5' end or the 3' end of the transcribed RNA, the ribozyme activity can be lost. In this case, one can place an additional trimming ribozyme, which functions in cis to perform the trimming on the 5' or the 3' side of the ribozyme portion, in order to precisely cut the ribozyme portion from the transcribed RNA containing the ribozyme (K. Taira et al., Protein Eng. 3: 733 (1990); A. M. Dzaianott and J. J. Bujarski, Proc. Natl. Acad. Sci. USA 86: 4823 (1989); C. A. Grosshands and R. T. Cech, Nucleic Acids Res. 19: 3875 (1991); K. Taira et al. Nucleic Acid Res. 19: 5125 (1991)). Multiple sites within the target gene can be cleaved by arranging these structural units in tandem to achieve greater effects (N. Yuyama et al., Biochem. Biophys. Res. Commun. 186: 1271 (1992)). By using such ribozymes, it is possible to specifically cleave the transcription products of the target gene in the present invention, thereby repressing the expression of said gene.

Endogenous gene expression can also be repressed by co-repression through the transformation by DNA having a sequence identical or similar to the target gene sequence. "Co-repression" refers to the phenomenon in which, when a gene having a sequence identical or similar to the target endogenous gene sequence is introduced into plants by transformation, expression of both the introduced exogenous gene and the target endogenous gene becomes repressed. Although the detailed mechanism of co-repression is unknown, it is frequently observed in plants (Curr. Biol. 7: R793 (1997), Curr. Biol. 6: 810 (1996)). For example, if one wishes to obtain a plant body in which the Hd6 gene is co-repressed, the plant in question can be transformed with a vector DNA designed so as to express the Hd6 gene or DNA having a similar sequence to select a plant having the Hd6 mutant character, i.e., a plant with reduced photoperiod sensitivity, among the resultant plants. The gene to be used for co-repression does not need to be completely identical to the target gene, but it should have at least 70% or more sequence identity, preferably 80% or more sequence identity, and more preferably 90% or more (e.g. 95% or more) sequence identity. Sequence identity may be determined by above-described method.

In addition, endogenous gene expression in the present invention can also be repressed by transforming the plant with a gene having the dominant negative phenotype of the target gene. A gene having the dominant negative phenotype means a gene which, when expressed, can eliminate or reduce the activity of the wild type endogenous gene inherent to the plant.

Vectors used for the transformation of plant cells are not limited so long as the vector can express inserted genes in plant cells. For example, vectors comprising promoters for constitutive gene expression in plant cells (e.g., califlower mosaic virus 35S promoter); and promoters inducible by exogenous stimuli can be used. The term "plant cell" used herein includes various forms of plant cells, such as cultured cell suspensions, protoplasts, leaf sections, and callus.

A vector can be introduced into plant cells by known methods, such as the polyethylene glycol method, electroporation, *Agrobacterium* mediated transfer, and particle bombardment. Plants can be regenerated from transformed plant cells by known methods depending on the type of the plant cell (Toki et al., (1995) Plant Physiol. 100: 1503–1507). For example, transformation and regeneration methods for rice plants include: (1) introducing genes into protoplasts using polyethylene glycol, and regenerating the plant body (suitable for indica rice cultivars) (Datta, S. K. (1995) in "Gene Transfer To Plants", Potrykus I and Spangenberg Eds., pp66–74); (2) introducing genes into protoplasts using electric pulse, and regenerating the plant body (suitable for japonica rice cultivars) (Toki et al (1992) Plant Physiol. 100, 1503–1507); (3) introducing genes directly into cells by the particle bombardment, and regenerating the plant body (Christou et al. (1991) Bio/Technology, 9: 957–962); (4) introducing genes using *Agrobacterium*, and regenerating the plant body (Hiei et al. (1994) Plant J. 6: 271–282); and so on. These methods are already established in the art and are widely used in the technical field of the present invention. Such methods can be suitably used for the present invention.

Once a transformed plant, wherein the DNA of the present invention is introduced into the genome, is obtained, it is possible to gain descendants from that plant body by sexual or vegetative propagation. Alternatively, plants can be mass-produced from breeding materials (for example, seeds, fruits, ears, tubers, tubercles, tubs, callus, protoplast, etc.) obtained from the plant, as well as descendants or clones thereof. Plant cells transformed with the DNA of the present invention, plant bodies including these cells, descendants and clones of the plant, as well as breeding materials obtained from the plant, its descendant and clones, are all included in the present invention.

The flowering time in plants with modified photoperiod sensitivity, prepared as above, is different from that of wild-type plants. For example, plants transformed with a DNA encoding the Hd6 protein have increased photoperiod sensitivity, and flowering time of the plant is delayed. On the other hand, plants wherein the expression of the DNA encoding the Hd6 protein is repressed due to the introduction of antisense DNAs, have reduced photoperiod sensitivity and the day-to-flowering of the plant is decreased. Thus, the time needed for flowering of plants can be regulated by controlling the expression of the Hd6 gene. According to the present invention, the heading date of rice, a valuable crop, can be closely controlled, which is extremely beneficial in the breeding of rice cultivars adapted to a particular environment.

Moreover, the present invention provides methods for assessing plant photoperiod sensitivity. According to the comparison of the Hd6 gene ORF of Kasalath, a functional allele of Hd6, and that of Nipponbare, a non-functional allele of Hd6, it was found out that only a nucleotide was substituted among the ORFs of these cultivars. The site encoding lysine in Kasalath is changed to a stop codon in the Hd6 gene ORF of Nipponbare by the substitution of a nucleotide. The stop codon in the Nipponbare gene prohibits translation of a functional product from the gene. This fact indicates that the expression of functional Hd6 proteins in a plant is one of the factors that determine the degree of photoperiod sensitivity of the plant. The method of assessing the photoperiod sensitivity of plants of the present invention is based on this finding and is characterized by the step of detecting whether a plant retains a DNA encoding a functional Hd6 protein.

The assessment of the photoperiod sensitivity of a plant based on whether the plant retains the DNA encoding a functional Hd6 protein or not can be performed on rice by detecting the mutation of the 2815th nucleotide "A" in the nucleotide sequence of SEQ ID NO: 2. Further, the restriction enzyme Hind III recognition site of the Kasalath Hd6 DNA is altered in that of Nipponbare so that the latter site cannot be recognized by the restriction enzyme Hind III, due to a difference in the nucleotide sequence of the Kasalath and Nipponbare Hd6 gene ORFs. The Hind III recognition site can be specifically detected in rice cultivars characterized as photoperiod sensitive cultivars by the existence of the photoperiod sensitivity E3 gene. Thus, the mutation of the nucleotide above can be detected by the presence or absence of recognition according to the restriction enzyme Hind III (CAPS (Cleaved Amplified Polymorphic Sequence) method). More specifically, the method using Hind III comprises the steps of: (a) conducting polymerase chain reaction using rice genome DNA as the template and primer pairs against the DNA consisting of the nucleotide sequence described in SEQ ID NO: 2 or a complementary strand thereof, which primer pairs are designed so as to contain, between them, the 2815th nucleotide "A" of the nucleotide sequence of SEQ ID NO: 2; (b) reacting the restriction enzyme Hind III with the DNA fragment amplified by the polymerase chain reaction in step (a); and (c) detecting whether the DNA fragments are digested by the restriction enzyme Hind III. Primers described in SEQ ID NO: 20 and 21 are examples of primer pairs that may be used in the above method. Whether the PCR product is digested by the action of the restriction enzyme Hind III or not can be determined by electrophoresis of the DNA fragments after treating them with the restriction enzyme, and detecting the pattern of electrophoresis. Subject plants whose PCR products are not digested with Hind III are determined to not possess a functional allele of Hd6.

In addition to the CAPS (Cleaved Amplified Polymorphic Sequence) method described above, the dCAPS method (Neff et al., The Plant Journal 14: 387–392, 1998) can be also used in the method of the present invention. The dCAPS method may be used in case where the site of nucleotide substitution does not correspond to the specific restriction enzyme recognition site. Specifically, primers are designed so that they hybridize to a sequence near the nucleotide substitution site, and a mismatch is introduced to a part of the primer so that a product amplified with the primer contains a new recognition site for a restriction enzyme. In fact, the present inventors used the primer "SEQ ID NO: 22/5'-CTTTGTGGAGGTCCAAACATTGTC-3'" as the primer including the mismatch, and primer "SEQ ID NO: 21/5'-CTACAGATCCACAGAACAGG-3'" as the primer common with that for the CAPS marker.

Additionally, the ASPCR (allele-specific PCR) method (Dan et al. Proc. Natl. Acad. Sci. USA 86: 2757–2760, 1989), wherein the primers are designed so that the 3' end of one of the primers corresponds to the nucleotide substitution site and no amplification product can be obtained for one of the cultivars, can be also used in the present invention.

The assessment of the photoperiod sensitivity of plants using the method of the present invention is effective, for example, in breeding plants by crossing. That is, when the introduction of photoperiod sensitive character is undesirable, crossing with plants having photoperiod sensitivity can be avoided by the present invention. On the contrary, when the introduction of a photoperiod sensitive character is desired, crossing with cultivars having photoperiod sensitivity is enabled by the present invention. Furthermore, the present method is also useful in selecting plants from crossed progeny plants. Determination of the photoperiod sensitivity of plants at the gene sequence is simple and reliable as compared to a determination based on the phenotype of the plant. Thus, the method for assessment of the photoperiod sensitivity of the present invention contributes markedly to progress in breeding methods for plants.

Further, the present invention provides DNAs comprising at least 15 nucleotides that are complementary to a DNA of the present invention consisting of the nucleotide sequence of SEQ ID NO: 2 or to the complementary strand thereof. Herein, the term "complementary strand" is defined as one strand of a double stranded DNA composed of A:T and G:C base pairs to the other strand. In addition, "complementary" is defined as not only those completely matching within a region of at least 15 continuous nucleotides, but also having a homology of at least 70%, preferably at least 80%, more preferably 90%, and even more preferably 95% or higher within that region. Such DNAs are useful as probes to detect or isolate a DNA of the present invention, or as primers to amplify a DNA of the present invention.

BRIEF DESCRIPTION OF THE DRAWINGS

FIGS. 4A–4H compares the nucleotide sequence of the candidate gene CKIIα of Nipponbare (SEQ ID NO: 5) with that of Kasalath (SEQ ID NO: 2).

FIG. 5 shows alignment of the predicated amino acid sequences of the CKIIα genes from rice maize, Arabidopsis, human, fly, and nematode (SEQ ID NOS: 23–28).

BEST MODE FOR CARRYING OUT THE INVENTION

Figure 1:
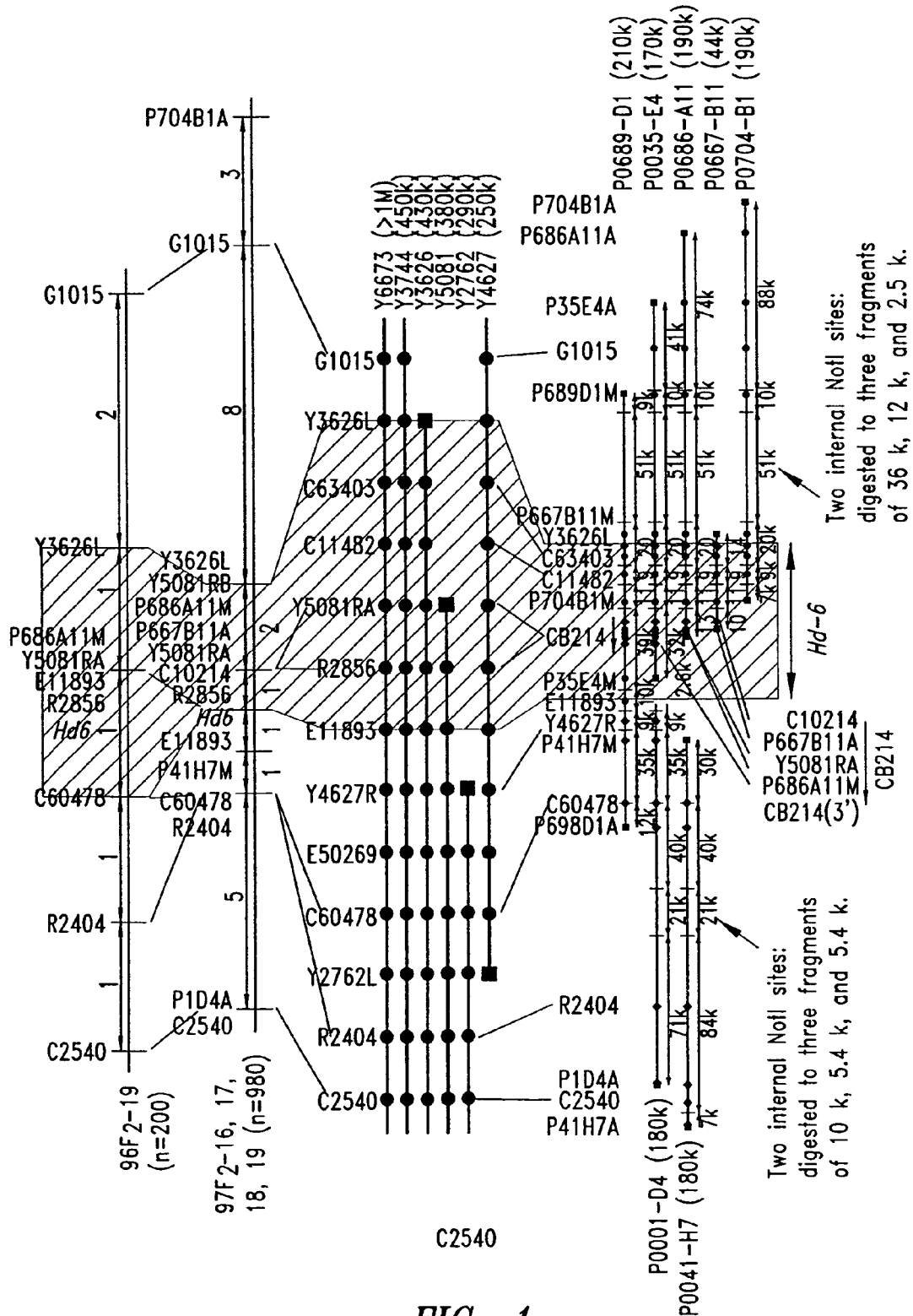
FIG. 1 schematically shows a linkage map around the Hd6 region, and a physical map aligning YAC and PAC.

The present invention is illustrated in detail below with reference to following examples but is not to be construed as being limited thereto.

EXAMPLE 1

Alignment of the Hd6 Gene Region by Linkage Analysis and Yeast Artificial Chromosome (YAC) Clones Advanced backcross progeny populations (1180 plants) of Nipponbare and Kasalath were grown on fields, and plants in which recombination had occurred near the Hd6 locus were selected as plants to isolate the Hd6 region. CAPS markers were used for efficient selection (Konieczny and Ausubel, Plant J. 4: 403–410 (1993)).

First, CAPS markers flanking the Hd6 gene region were constructed from RFLP markers, R2404 and C1329. The resulting products show polymorphism when R2404 is amplified by PCR using primers, "SEQ ID NO: 6/5'-GCAAAATGCCACTTTGTGGC-3'" and "SEQ ID NO: 7/5'-AACTTACGCTCAAATCAAAA-3' (antisense)", specific to the cDNA clone R2404, under the condition of: 94° C. for 2 minutes; 40 cycles of "94° C., 30 seconds; 58° C., 30 seconds; and 72° C., 1 minute"; and 72° C. for 7 minutes. On the other hand, polymorphism of C1329 is detected by conducting PCR using primers specific to C1329, "SEQ ID NO: 8/5'-TGTTGCCCTCATTATCTGCT-3'" and "SEQ ID NO: 9/5'-GGAGGTCGGAGTAAAGGAAA-3' (antisense)" under the condition of: 94° C. for 2 minutes; 35 cycles of "94° C., 1 minute; 60° C., 2 minutes; and 72° C., 3 minutes"; and 72° C. for 7 minutes, and then, digesting with a restriction enzyme Eco T22I. Template DNAs used for PCR were extracted according to a modified method of Manner and Tenning (Plant Mol. Biol. Reptr. 15: 38–45 (1997)). More specifically, 2 to 3 cm long pieces of leaves were crushed in extraction buffer (100 mM Trsi-HCl (pH 8.0), 50 mM Na-EDTA, 1.25% SDS, 0.38% sodium bisulfate, 200 μg/ml proteinase K); the solution was centrifuged after incubation at 65° C. for 2 hours. The supernatant was treated with isopropanol, and then the precipitate was dried and dissolved in an appropriate amount of water. 40 plants in total were selected as recombinants, wherein recombination occurred between the CAPS marker R2404 and C1329.

DNA was extracted from selected plants, and RFLP markers near the Hd6 gene were used to construct a detailed linkage map. The genotype of the Hd6 gene locus was determined by a progeny test. More specifically, selfed progeny of selected plants were grown on fields and the genotype was determined from the distribution of the days-to-heading of respective plants of respective lines. The Hd6 gene was demonstrated to exist between the RFLP marker R2404 and G1015, and was determined to co-segregate with R2856.

Using the detailed linkage map, a detailed alignment map was constructed on the basis of information from an alignment map of YAC clones prepared in the Rice Genome Research. All markers used for the linkage map were confirmed to be contained in respective YAC clones by Southern hybridization and PCR using STS primers of respective markers. Additionally, DNA end-fragments of YAC clones existing on the Hd6 region and cDNA clones existing on respective YAC clones were similarly analyzed.

During the analysis, contrary to other markers, R2856 could be detected in YAC clones existing on the Hd6 region by Southern hybridization, but, according to the result of PCR, was identified as a marker not existing on that YAC. This result suggests that a region highly homologous to the R2856 marker and to which the R2856 marker hybridizes exists on the candidate region of Hd6 gene; however, a gene encoding the cDNA clone R2856 does not exist therein. That is, the R2856 is an RFLP marker that has an extremely high homology with the sequence in the Hd6 region, but is originally encoded by a gene existing on other regions of the genome.

PCR analysis was conducted using R2856 specific primers, "SEQ ID NO: 10/5'-AGCACTCAAAAACACCAAGC-3'" and "SEQ ID NO: 11/5'-AACAAAGATACAAACAG-CAC-3' (antisense)", under the following condition: 94° C. for 2 minutes; 30 cycles of "94° C. for 1 minute, 60° C. for 2 minutes, and 72° C. for 3 minutes"; and 72° C. for 7 minutes.

C10214 (Ac. No. D22035) was identified as a clone having high homology with R2856 from EST clones of Nipponbare (DDBJ (DNA Data Bank of Japan), which clones were analyzed in the Rice Genome Research Program. PCR was conducted under the same condition as above with C10214 specific primers, "SEQ ID NO: 12/5'-CTTGATCCTCAGCTTGAAGCT-3'" and "SEQ ID NO: 13/5'-TGCAAGGCTACAAGCACATTC-3' (antisense)", to confirm the existence of a gene encoding C10214 on the Hd6 region. As a result, it was demonstrated that the gene encoded by the clone exists on the Hd6 region.

Further, a more detailed linkage map was constructed based on the detailed alignment map of YAC clones using respective YAC DNA end-fragments and cDNA clones on the YAC clone as the RFLP markers. The result demonstrated the Hd6 gene region to exist between the marker E11893 and Y3626L (FIG. 1).

Example 2

Alignment of Hd6 Gene Region Using P1 Derived Artificial Chromosome (PAC) Clones STS primers were prepared from the nucleotide sequence of ESTs and YAC end-fragments near the Hd6, C10214, E11893, Y3626L, C63403, C11482, and C60478, to screen the Nipponbare PAC genomic clone library (8352 clones, average insert length 112 kb). Conversion into STS was conducted with primers SEQ ID NO: 12 and 13 (described above) for C10214; "SEQ ID NO: 14/5'-TCGTCGCGCT-CATAGCTAGA-3'" and "SEQ ID NO: 15/5'-ACTTC-CTCGCTATGCCACAG-3'(antisense)" for E11893; and "SEQ ID NO: 16/5'-GCCCATAATGATACGATATACT-3'" and "SEQ ID NO: 17/5'-TGGTGGTGGTTGCTGTTCGA-3'" for Y3626L. Primers for EST mapping generated by the Rice Genome Research Program were used for C63403, C11482, and C60478. The condition for PCR was: 94° C. for 2 minutes; 35 cycles of "94° C. for 30 seconds, 60° C. for 1 minute, and 72° C. for 1 minute"; and 72° C. for 7 minutes. As a result, 7 clones expected to include genomic fragments near the Hd6 were selected. Further, end-fragments of these clones were used as a probe for RFLP analysis to reveal that PAC clone P689D1 comprised all the candidate gene region of Hd6.

Example 3

Determination of the Candidate Gene Region by Nucleotide Sequence Analysis

Figure 2:
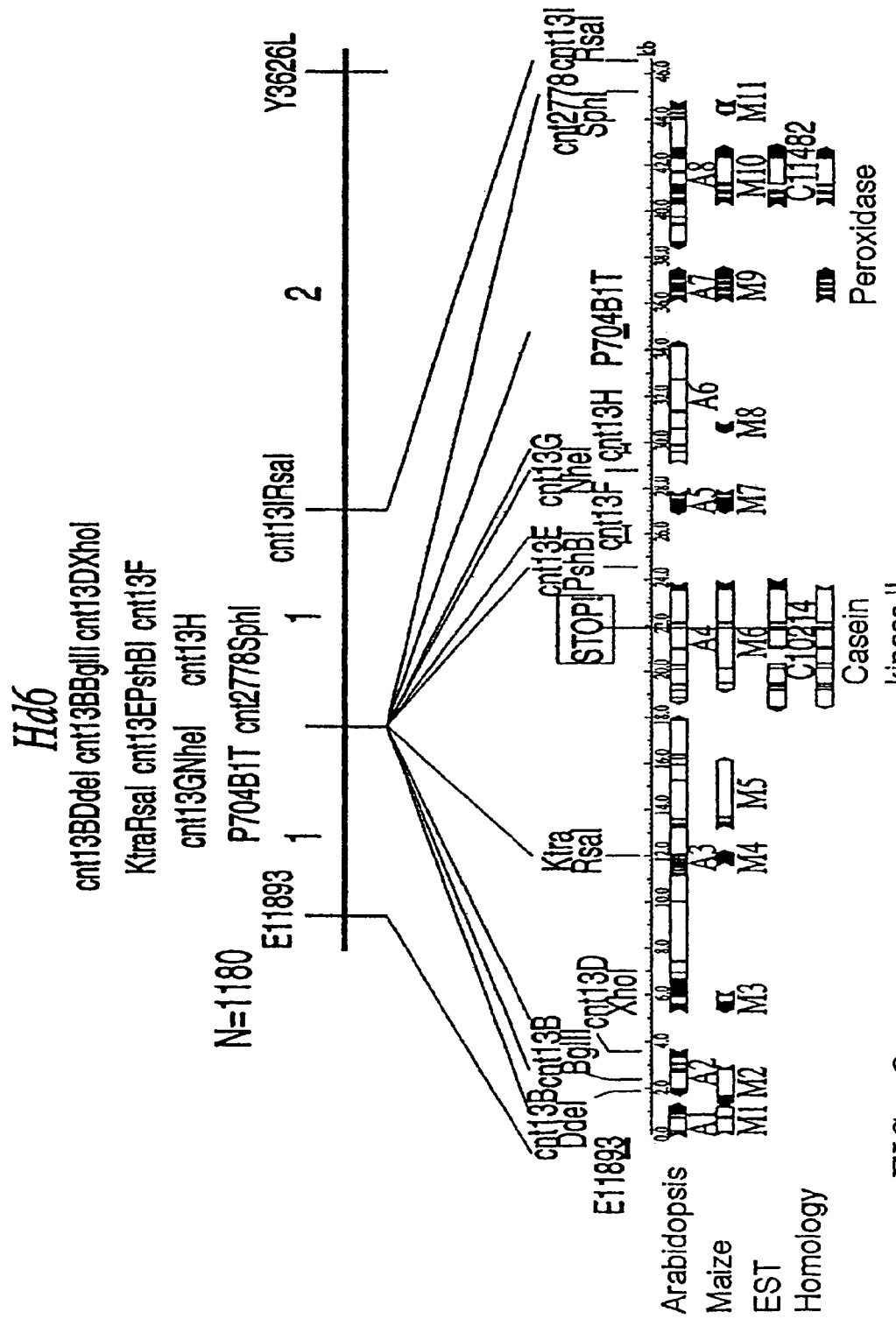
FIG. 2 schematically shows the presumed genes on the candidate genomic locus.

Nucleotide sequence analysis of PAC clone P0689D1, which is expected to contain the Hd6 gene, was performed. To analyze the nucleotide sequence, insert DNA (including the vector) of P0689D1 was fragmented with ultrasonication to prepare a sublibrary with an average insert length of 2 kb to 5 kb. Nucleotide sequences of 2000 clones randomly selected thereof were analyzed and were assembled using the computer software Phred/Phrap. New CAPS markers were produced according to the nucleotide sequence information of the candidate gene region specified by linkage analysis to delimit the candidate region where the candidate gene exists to a region of about 47 kb. Gene prediction by the computer program GENSCAN and BLAST homology search of nucleotide sequence of the candidate region revealed a region with extremely high homology with the CKIIα gene of *Arabidopsis*. Additionally, the nucleotide sequence of the region was concordant with that of the EST clone C10214 (FIG. 2). The CKIIα gene of *Arabidopsis* is demonstrated to influence the expression of several genes which expression is regulated by light (Lee et al. Plant Physiol. 119: 989–1000 (1999)), and to activate the circadian clock gene CCA1 protein by phosphorylation (Sugano et al. Proc. Natl. Acad. Sci. USA 95: 11020–11025 (1998)).

Example 4

Fine-Scale Linkage Analysis

Figure 3:
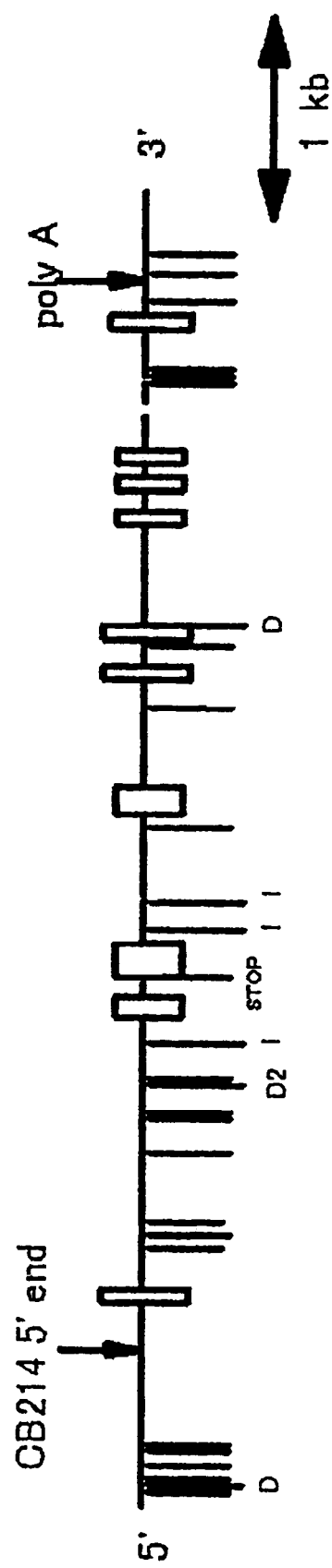
FIG. 3 schematically shows a fine-scale genetic map around the Hd6 region.
Figure 6:
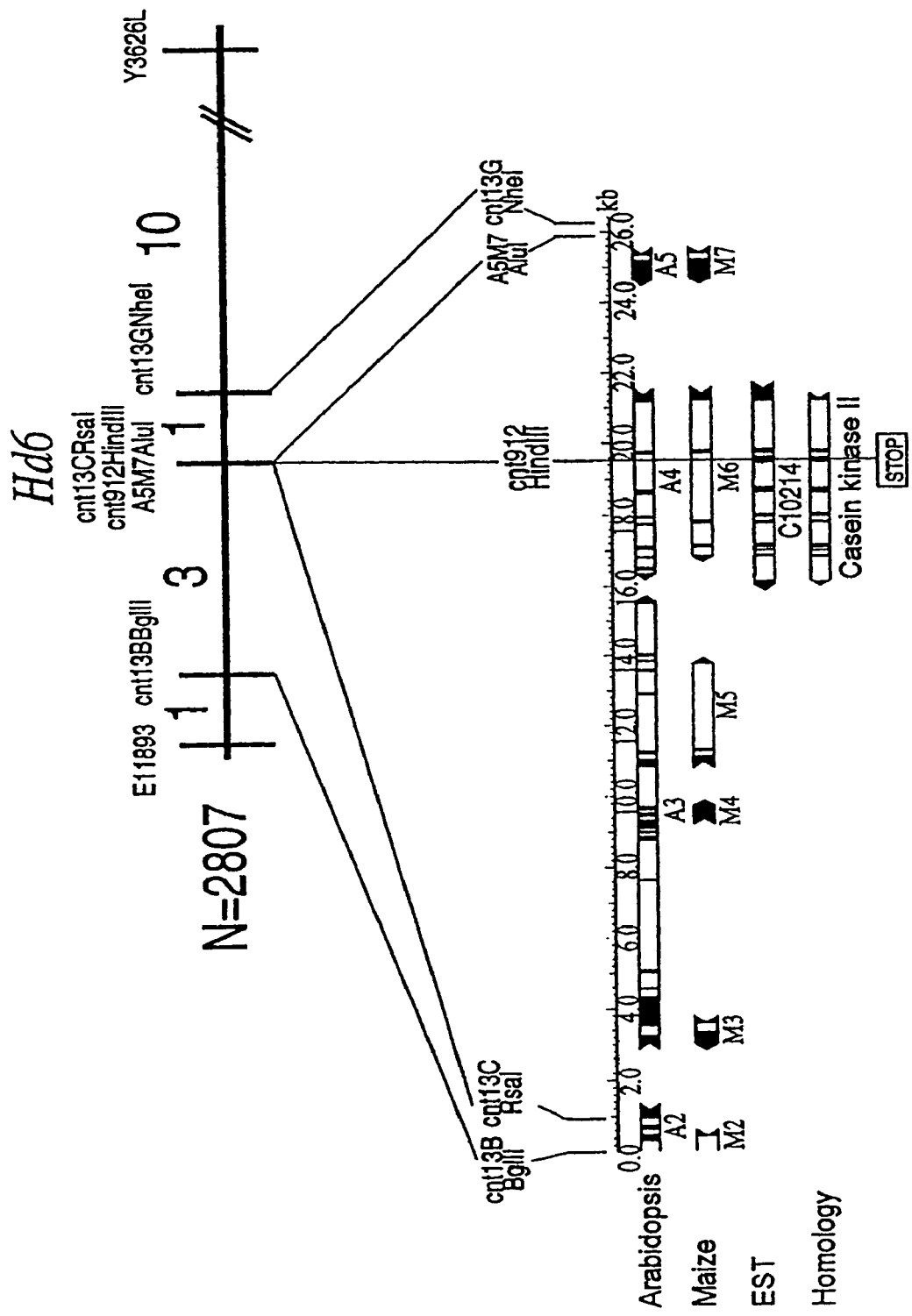
FIG. 6 schematically shows the presumed gene on the candidate genomic locus.

A large population was subjected to linkage analysis to more precisely determine the Hd6 gene candidate region. Plants having recombination between CAPS markers R2404 and G1015, markers that flank the Hd6 gene, were newly selected from a segregating population of 1627 plants according to the method described above. Polymorphism of the clones was analyzed by PCR using G1015 specific primers "SEQ ID NO: 18/5'-CTGCAAGTTCAAGC-CGATCA-3'" and "SEQ ID NO: 19/5'-TTGCAATTG-GCTAAGCAAGAC-3'", under the condition: 40 cycles of "94° C. for 40 seconds, 65° C. for 40 seconds, and 72° C. for 90 seconds", and 72° C. for 7 minutes; followed by digestion of the obtained amplification product by the restriction enzyme Hae III. 11 plants were newly selected as plants with recombination in the Hd6 candidate gene region (between E11893 and Y3626L). DNA was extracted from these plants, and a detailed genetic map was made using CAPS markers together with the 4 recombinant plants identified by the former linkage analysis. The CAPS markers were prepared based the nucleotide sequence analysis described below. The genotype of Hd6 gene locus was determined by the progeny test as described above. The result demonstrated the Hd6 gene to be located between the CAPS marker, cnt13GNheI and cnt13BBglII; and to cosegregate with cnt13CRsaI, cnt912HindIII, and A5M7AluI (FIG. 3). The candidate region of Hd6 gene was mapped on a genomic region of 26.4 kb.

Example 5

Comparison Between the CKIIα Gene Nucleotide Sequences of Kasalath and Nipponbare The genomic nucleotide sequence of the CKIIα gene of Kasalath was determined using the nucleotide sequence information of the CKIIα gene of Nipponbare, which, in turn, was determined by analysis of the PAC clone. More specifically, primers enabling amplification of specific region of the candidate gene were prepared, fragments were amplified using Kasalath genomic DNA as the template, and were cloned to analyze the nucleotide sequence. Nucleotide sequence was analyzed by changing the primers so as to hybridize to a nearby sequence to determine the entire nucleotide sequence around the CKIIα gene. Comparison of the Kasalath and Nipponbare CKIIα genes revealed multiple substitution, deletion and insertion of nucleotides, but only one of the nucleotide substitutions was in the ORF. The substitution results in a stop codon in Nipponbare, whereas the site encodes a lysine in Kasalath (FIGS. 4A–4H; SEQ ID NO: 2). It is considered that the CKIIα gene encodes a functional protein of 333 amino acids in Kasalath, whereas it cannot be translated as a functional product in Nipponbare due to the existence of the stop codon.

Example 6

Expression Pattern Analysis of the Candidate Gene, CKIIα

Figure 7:
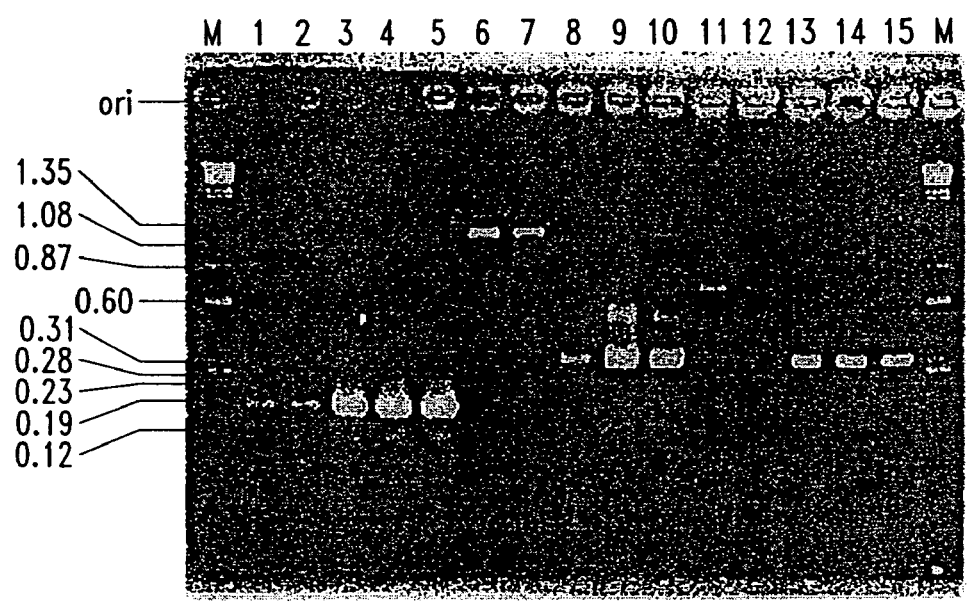
FIG. 7 is an electrophoretogram showing the expression pattern of the candidate gene CKIIα analyzed by RT-PCR. "M" indicates the marker (λ/Hind III+φX174/Hae III). Templates used for respective lanes were as follows: lane 1, 6, and 11, total DNA of Nipponbare; lane 2, 7, and 12, total DNA of Hd6 NIL; lane 3, 8, and 13, total RNA of Nipponbare; lane 4, 5, 9, 10, 14, and 15, total RNA of Hd6 NIL. PCR primers used for the amplification in lane 1 to 5 were for actin gene amplification; those in lane 6 to 10 for C10214 (CKIIα on the same locus as Hd6) amplification; and those for lane 11 to 15 for R2856 (CKIIα on a different locus to Hd6) amplification.

The difference in the expression level of the candidate CKIIα gene in Nipponbare, which is supposed to lack the photoperiodic sensitivity gene Hd6, and near isogenic lines of Nipponbare, that has the Kasalath Hd6 gene, was analyzed by RT-PCR. The nucleotides described above as SEQ ID NO: 7 and 8 were used as primers. The condition for PCR was as follows: 94° C. for 2 minutes; 25 cycles of "94° C. for 30 seconds, 62° C. for 40 seconds, and 72° C. for 1 minute"; and 72° C. for 7 minutes. As a result, no difference in the expression level of actin gene and CKIIα gene existing in other region than Hd6 could be detected, whereas the expression level of the candidate CKIIα gene was markedly low in Nipponbare compared to Hd6 near isogenic lines (FIG. 7).

Example 7

Method for Evaluating Photoperiod Sensitivity in Rice Cultivars

Figure 8:
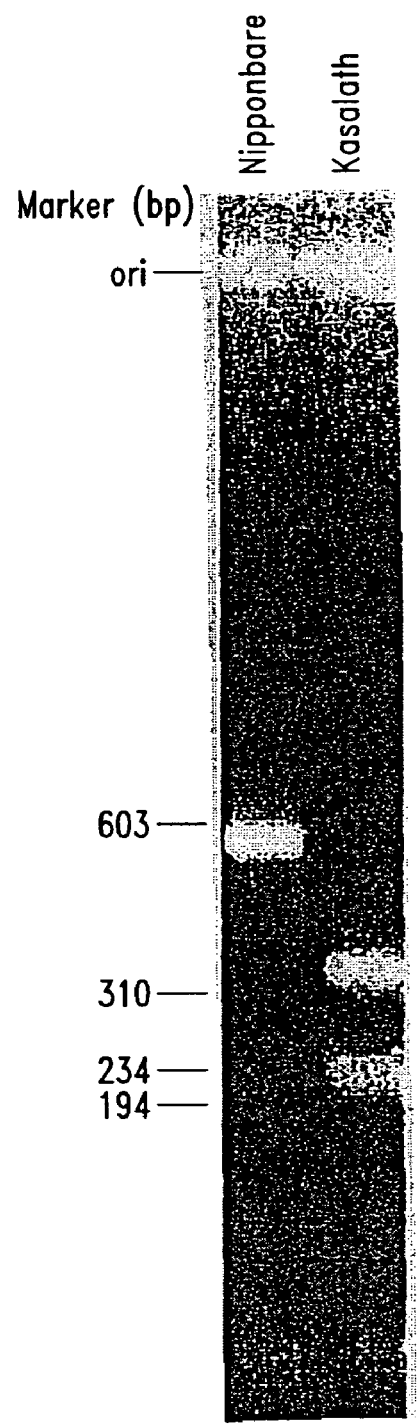
FIG. 8 is an electrophoretogram showing the polymorphism between the genomic DNA of Nipponbare and that of Kasalath detected by the CAPS method.

Among the photoperiod sensitivity genes whose existence has been genetically demonstrated, the E3 gene has been suggested to exist on chromosome 3. Therefore, the relationship between E3 and Hd6 was demonstrated using a simple method for identifying differences in the nucleotide sequence of Hd6 coding region in Nipponbare and Kasalath. The mutated nucleotide site (substitution of the 2815th nucleotide from "A" to "T" in SEQ ID NO: 2) existing on the Hd6 gene of Nipponbare and Kasalath is within the recognition site of a restriction enzyme Hind III, and the inventors revealed that the Hd6 gene is digested in Kasalath but not in Nipponbare. Thus, a DNA fragment of 543 bp, including the mutated nucleotide site, was amplified with primers, "SEQ ID NO: 20/5'-ACCTGGCAGCATGTTAT-GAC-3' (sense, first intron)" and "SEQ ID NO: 21/5'-CTACAGATCCACAGAACAGG-3' (antisense, third intron)". When the amplified DNA fragment has the Kasalath sequence (without a stop codon), the fragment is digested by the treatment with the restriction enzyme Hind III into two fragments with lengths of 329 bp and 214 bp; those with other sequences could not be digested (FIG. 8). Thus, it was indicated that the method could be used for identifying genes that confer photoperiod sensitivity to plants. Next, the efficiency of the method was tested using cultivars, wherein the existence or absence of the E3 gene has been already proven by genetic analysis (Okumoto et al. International Rice Research Institute, Rice Genetics II pp. 778–780 1991). The fragments amplified from the genes of 8 cultivars, which were demonstrated to lack the E3 gene, were not digested, whereas those of other 8 cultivars that were shown to have the E3 gene were digested (Table 1).

TABLE 1

| Cultivar | genotype | CAPS analysis |
| --- | --- | --- |
| Kinmaze | E3 | + |
| Koshihikari | e3 | − |
| Manryo | e3 | − |
| Nipponbare | e3 | − |
| Nakateshinsenbon | E3 | + |
| Hoyoku | E3 | + |
| Akebono | E3 | + |
| Norin 6 | e3 | − |
| Fujiminori | E3 | + |
| Fujisaka 5 | E3 | + |
| Kiyonishiki | e3 | − |
| Norin 1 | e3 | − |
| Norin 8 | e3 | − |
| Shiranui | E3 | + |
| Norin 22 | e3 | − |
| Zuiho | E3 | + |

Genotype E3: photoperiod sensitivity gene E3
Genotype e3: lacking photoperiod sensitivity gene E3
CAPS analysis +: including the Hind III recognition site, and is digested with Hind III.
CAPS analysis −: lacking a Hind III recognition site, and isn't digested with Hind III.

Thus, the possibility that the Hd6 gene corresponds to the E3 gene is extremely high, and it is conceivable that the newly developed method to detect the stop codon of the present invention is an efficient tool to assess the photoperiod sensitivity of Hd6 or E3 genes.

Example 8

Production of Transgenic Plants Expressing the Hd6 Gene and Date-to-Heading Thereof A genomic fragment (Nhe I-Bgl II 8.9 kb) comprising the CKIIα gene of Kasalath, which gene was considered to be the candidate gene of Hd6, was inserted into the binary vector pPZP2H-lac to produce a plasmid pPZPCKII-10A. Then, Nipponbare was transformed with the plasmid using *Agrobacterium*. No apparent difference could be detected in the transformed generation (T0), because the timing of shoot regeneration did not match between plants transformed with the vector alone and those transformed with pPZPCKII-10A. Thus, the selfed progeny of the two transformed plants as well as Nipponbare, near isogenic lines of Hd6 [NIL (Hd6)], and selfed progeny of the plant transformed with the vector alone were seeded in a closed growth chamber (Tsukuba, Ibaraki) on May 16 to investigate the heading date of respective plants. The number of plants whose first panicle had appeared where every two days (Table 2).

The heading dates of progenies of plants transformed with the candidate gene showed segregation, the plants of early heading had a transgene and the plants showing late heading did not have a transgene. The heading date of early and late heading plants were almost the same as those of Nipponbare and NIL (Hd6), respectively. The heading date of all progenies of plants transformed with the vector alone were the same as those of Nipponbare. These results strongly suggest that the candidate CKIIα gene has the function of the Hd6 gene to delay the heading date under natural field condition.

TABLE 2

| | heading date | | | | | | | | | | | | |
|---|---|---|---|---|---|---|---|---|---|---|---|---|---|
| | 93 | 95 | 97 | 99 | 101 | 103 | 105 | 107 | 109 | 111 | 113 | 115 | 117 |
| Nipponbare | 3 | 6 | 1 | | | | | | | | | | |
| NIL (Hd6) | | | | | | | 1 | 3 | 4 | | | | |
| vector alone | 3 | 6 | 2 | | | | | | | | | | |
| pPZPCKII-10A transformant 1 | 1* | | 1* | | | | | 8 | 3 | | | | |
| pPZPCKII-10A transformant 2 | 1* | | | | | | | 1 | 2 | 1 | 1 | | 1 |

*indicates plants without pPZPCKII-10A

INDUSTRIAL APPLICABILITY

The present invention provides photoperiod sensitivity genes in rice cultivars. The genes of the present invention confer photoperiod sensitivity to rice plants and may be used to control the heading date of rice. Therefore, the genes may be very useful in breeding. The heading date of rice plants can be changed by the use of the genes of the invention. Thus, the genes are particularly useful for breeding rice cultivars adapted to particular locations and seasons to grow the plant. Furthermore, the method to breed rice cultivars using a gene of the present invention is beneficial as compared to conventional methods, in that an object plant can be obtained in a short period with high reliability.

Further, the present invention provides methods for assessing the photoperiod sensitivity of plants. Two to three years of exceeding labor was needed to determine the photoperiod sensitivity of one cultivar according to conventional assessment methods which consist of: crossing object cultivars with test plant lines to identify the existence of a specific gene; and then, determining the existence of the gene by the segregation of the heading date in the progeny of the plants. According to the present method, the photoperiod sensitivity of a plant can be determined by: only (1) harvesting a part of the seedling about 2 weeks after seeding; (2) extracting the DNA thereof; and (3) determining after PCR using the DNA as the template and restriction enzyme treatment. The degree of photoperiod sensitivity of progenies of plants can be determined prior to crossing, based on the presence or absence of the gene, which is a valuable information for selecting and screening parent plant to be crossed. Furthermore, the presence or absence of the photoperiod sensitivity gene in each selected plant can be easily determined using the methods as described above. Thus, the gene serves also as selection markers.

The invention claimed is:

1. An isolated DNA encoding the protein comprising the amino acid sequence of SEQ ID NO: 1.

2. A vector comprising the DNA of claim 1.

3. A plant cell transformed with the vector of claim 2.

4. A plant transformant comprising the plant cell of claim 3.

5. The plant transformant of claim 4, wherein said plant transformant is rice.

6. A plant transformant which is a progeny plant or a clonal plant of the plant transformant of claim 4 and wherein the progeny plant or clonal plant comprises the vector of claim 2.

7. A breeding material of the plant transformant of claim 4 comprising the DNA of claim 1.

8. A method for producing a plant transformant, which comprises the following steps of:
(a) introducing the DNA of claim 1 into a plant cell, and
(b) regenerating a plant transformant from the plant cell.

9. A method for increasing the photoperiod sensitivity of a plant, said method comprising introducing into said plant the DNA of claim 1.

10. The method of claim 9, wherein flowering in said plant is delayed compared to a wild-type plant.

11. The method of claim 9, wherein the plant is rice.

12. An isolated host cell comprising a vector, said vector comprising the DNA of claim 1.

* * * * *

UNITED STATES PATENT AND TRADEMARK OFFICE
CERTIFICATE OF CORRECTION

PATENT NO. : 7,038,110 B1 Page 1 of 1
APPLICATION NO. : 10/129357
DATED : May 2, 2006
INVENTOR(S) : Masahiro Yano et al.

It is certified that error appears in the above-identified patent and that said Letters Patent is hereby corrected as shown below:

Title Page
Item (56) Other Publications:
  Kikuchi, Y., "Types in" should read as --Types and in--
  Martienssen, R., "Biologyu" should read as --Biology--
  Datta, S.K., "Regeneratiion" should read as --Regeneration--
  Christou, P. et al., "Indicia" should read as --Indica--
  Wu, D. et al., "βGlobin" should read as --β -Globin--

Signed and Sealed this

Nineteenth Day of December, 2006

JON W. DUDAS
*Director of the United States Patent and Trademark Office*

SEQUENCE LISTING

```
<160> NUMBER OF SEQ ID NOS: 28

<210> SEQ ID NO 1
<211> LENGTH: 333
<212> TYPE: PRT
<213> ORGANISM: Oryza sativa (Kasalath)

<400> SEQUENCE: 1

Met Ser Lys Ala Arg Val Tyr Ala Asp Val Asn Val Leu Arg Pro Lys
  1               5                  10                  15

Glu Tyr Trp Asp Tyr Glu Ala Leu Thr Val Gln Trp Gly Glu Gln Asp
                 20                  25                  30

Asp Tyr Glu Val Val Arg Lys Val Gly Arg Gly Lys Tyr Ser Glu Val
             35                  40                  45

Phe Glu Gly Ile Asn Val Asn Asn Asn Glu Lys Cys Ile Ile Lys Ile
         50                  55                  60

Leu Lys Pro Val Lys Lys Lys Ile Lys Arg Glu Ile Lys Ile Leu
 65                  70                  75                  80

Gln Asn Leu Cys Gly Gly Pro Asn Ile Val Lys Leu Leu Asp Ile Val
                 85                  90                  95

Arg Asp Gln His Ser Lys Thr Pro Ser Leu Ile Phe Glu Tyr Val Asn
            100                 105                 110

Asn Thr Asp Phe Lys Val Leu Tyr Pro Thr Leu Thr Asp Tyr Asp Ile
            115                 120                 125

Arg Tyr Tyr Ile Tyr Glu Leu Leu Lys Ala Leu Asp Tyr Cys His Ser
```

```
        130             135             140
Gln Gly Ile Met His Arg Asp Val Lys Pro His Asn Val Met Ile Asp
145                 150                 155                 160

His Glu Leu Arg Lys Leu Arg Leu Ile Asp Trp Gly Leu Ala Glu Phe
                165                 170                 175

Tyr His Pro Gly Lys Glu Tyr Asn Val Arg Val Ala Ser Arg Tyr Phe
            180                 185                 190

Lys Gly Pro Glu Leu Leu Val Asp Leu Gln Asp Tyr Asp Tyr Ser Leu
        195                 200                 205

Asp Met Trp Ser Leu Gly Cys Met Phe Ala Gly Met Ile Phe Arg Lys
210                 215                 220

Glu Pro Phe Phe Tyr Gly His Asp Asn His Asp Gln Leu Val Lys Ile
225                 230                 235                 240

Ala Lys Val Leu Gly Thr Glu Ala Leu Asn Ala Tyr Leu Asn Lys Tyr
                245                 250                 255

His Ile Glu Leu Asp Pro Gln Leu Glu Ala Leu Val Gly Arg His Ser
            260                 265                 270

Arg Lys Pro Trp Ser Lys Phe Ile Asn Ala Asp Asn Gln His Leu Val
        275                 280                 285

Ser Pro Glu Ala Val Asp Phe Leu Asp Lys Leu Leu Arg Tyr Asp His
    290                 295                 300

Gln Asp Arg Leu Thr Ala Arg Glu Ala Met Ala His Pro Tyr Phe Leu
305                 310                 315                 320

Gln Val Arg Ala Ala Glu Asn Ser Arg Ala Arg Pro Gln
                325                 330

<210> SEQ ID NO 2
<211> LENGTH: 6930
<212> TYPE: DNA
<213> ORGANISM: Oryza sativa (Kasalath)

<400> SEQUENCE: 2
cacactattg gcctggcctt agtgccagaa cctgttatt tcttctgttt tatagtctga      60
tgcattttg ttaatggaaa tggagggcct ttttcccttc gataaaaaaa atgtatgaga     120
ttattagtta attatggtag tattgaaaaa tataccacga taaaaaaaac ttaaaatcaa     180
attaaaatta attttcaaca tttatatttt agctacgggt gataagtcaa acacaaaca     240
acggtctttg tacgtaagtc ttttcaaaa cttgtggtaa acattcttcg ttcagttatt     300
aatatttgat gtttaggaca agatctgatc aaacttctaa aattctaaca aatcaattcc     360
atattaaatt aagtttatga agcgctataa gcttgtgatt ttatgatagc acttgttgag     420
ataaatatat gtatatcttt tatcttatct ttaaactaag tagaggtatt tgttaaatta     480
ttgatgatca gaaatttaaa aagttcgacc atatcttgta ctagtactaa acgtaaaata     540
tttttgacta aaggaagtaa ttaaaattta agaggcaaaa ttacgtgtga atttgagaag     600
acttccaatt caacagctca atgatcggga cacattctta aaaagaaaaa aaagaaaca     660
aaaaagatcc ggacacgcat gcgcaaatgg agctttcata ggcagaaggc gtaatcaact     720
ggaaggcgtc ttctcctgga gggaaaggtc gggcccacgt aagggaacaa accacctgt     780
cagtgaccaa aagccagcag attccagagt cgccgtccca cgccgcctct atctatctcc     840
acgtgaaata aaaaaaaaac aaagctcccg aaaatattct ctctccccca ccccgaaac     900
cctagcgcga cctcgccgcc ggcaatggcc gcatgaccga tgcgcctccg ccaggagcc     960
gcccgcaccc acccagcagc agcgtcgccg tgcccgccgc cgcggcggca gtgatcgcag    1020
```

```
ccgccctcgc gtcctccttc ctcgccctgc tgcagccgcc ccggcgcgcc ccggtcgccg    1080
cgggatccag ggtcggcatg tcgaaggcga gggtctacgc cgacgtcaac gtgctgcgcc    1140
ccaaggagta ctgggactac gaggcgctca ccgttcaatg ggggtaggta gcacagccag    1200
ccagctgacg tcaccttcct gagcccctg atcagcggcc gtagcttgta ttctccagat     1260
ttagttcgcg atccgtatcc cgtacacctg gctgggttt gcttattggg attaggttgg     1320
attattgggt tatgcgtagg tttgcttgtg cctgtagatt ttggttttgg tcagggaatt    1380
gggaatttat tgtggcttga aggttagatt gaattgcttc tgtttctatt aggacgaact    1440
caataccgaa gactgcttta gtagttttac atgtttgtac tataggagta ggggacacat    1500
gtttaccgaa tggttgaaga aactgttatg aatttgcaag gttatgattt taattttgga    1560
atcaatctca ctatatcttc cttttaaagt tgatactagt gttgttcagt taagagcctt    1620
tgtttgattg tgaatggcaa gctgtaggta ttgatcctat ttttgttggg gataaaatct    1680
aagttaaggc aaaattaggc agttttatgt ttaatcattg gaacaaagta agttggtgat    1740
gggtttctgg gtgtttcttt tgcatcatct gataaccaag attgatgagt aaagcataac    1800
ttggtagtat agtgctttgg gcctaatctt ctttagcact gaacattcac caagttctat    1860
gcttttatgt aatctcaatt ttaacattgt gttttccttc actcacccta gaatatacta    1920
cctgaaagca atcaatgaaa tcaaatataa cttcgtttct acctatatga ttgtaacatg    1980
ctgagtaata tggtgccaaa caactcaaca catataatac tgtccttaac aacccatctt    2040
cttttccctg tagaagttgc agccctagta tattctgtac atgtcatgct acctagatga    2100
caattgaggc ctggtaggag tgtgcttgtt taattttggt actccaaaag tgcactgttt    2160
ttctcaatct gactctgtta ccagttgtgt ttcctctaga tgtattcctt atctatggtg    2220
aattattaaa taagttgtct ggtgacaaaa aagaaaaaga aaagaaaag aagagatgaa     2280
caatatgtag ctcattgatg atcccttgtc tgcttgaact ttatgagaaa ctatagaaag    2340
cagtggtgtt ttccctgacc tgatgttaaa tacttgttaa gaattgagct ttcttcgaag    2400
tttgttcagt ttacacacca acactaagaa ttgccatata tctccatctt ttgtccattt    2460
aattcttgtt acctcaagtc attgagggac ctggcagcat gttatgactt acacaatacc    2520
tcgctaacta ttatggtgca tctttaacag tgagcaggat gactatgaag ttgtcaggaa    2580
agttggaaga ggtaaatata gtgaagtctt tgaaggcatc aatgttaaca acaatgagaa    2640
atgcatcatc aagatactca agcctgtgaa gaaaaagaag gtatttaatt gatcttattg    2700
actgtttttt ttaattgcta gtgttgaagt tcttaaccta cctttcatat gtttgaacag    2760
atcaaaaggg agattaaaat acttcagaat cttttgtggag gtccaaacat tgtgaagctt    2820
cttgatattg tcagagatca acattctaag actcctagct tgatctttga atatgtcaac    2880
aatacagact tcaaagtgct gtaccccacg ttgacagatt atgatatccg ctactacata    2940
tatgagctac tcaaggtctt cattgagcct tcattgtcat ccctatttat ttactctatt    3000
cagtaaaaca tcctgttctg tggatctgta gaatgatgta tctcttatag aaattgtttc    3060
acaattactt tcctattatg tgaagatcca actaaacaca cttgtaatat atcctagaca    3120
aatatcacca ttctcactgc ttgcaagttg caacatatct ttaattattt atgtatgtat    3180
gaacttgatt attttctaag ttacatggct taaaacttgt cacaatctca agcagtttat    3240
ggatcagttt tgttttgagt tttaattata gtagcatctt gcacttcata atgtacagat    3300
gacaaaagaa ttcctgaatt gcatatgtgc tataatggtt tatgatctgg gattttgaag    3360
```

```
agaagtgtcg ttttatacat ttctaagttc agcactatgt tggtgttaag aattcagcca   3420
tcaatgggca tcttaacgta tgtgctaggt catgccttct atccatgggt aataaactgt   3480
taacacacag tgtgtgtttt tcatatcgat attcttagcc aagaacagta gcatcatttg   3540
cccttaatcc tgtgtgttaa gtttgtttaa cgaatctagt tgattttctt tacaatattt   3600
tccttctgtt tatggcccca ggcattagac tactgccatt cacaaggcat tatgcatcga   3660
gatgtcaagc cccacaatgt tatgatagat catgagctcc gaaaacttcg attgatagac   3720
tggggcctgg ctgagttcta tcatccaggg aaggaatata atgttcgtgt tgcttcaagg   3780
ttggtgtagt tacaagcaaa ctacttgttt ggttatgatt ttcttgcttt tttattgaat   3840
tggattgcac cctgataatc acttgaatca tgagaggaag ctaacttaag aaggtagcat   3900
ccctgttttg cagtttgttt gctaacttgg ctctagaagc aatacgtgaa ccgataaatt   3960
acttggtttg aattcactgc tactgttgaa gtctgaattg cctagtggtc cttttgcaac   4020
attaatgtta cgaaatgctg aaagttaagc aatgaagctg tttaccctta aacaactaag   4080
tttacgtctg aaaaaaggc aataaaacag ataccattac tagccccttta ttattttgt   4140
aagcatgtta tcactggagt atatcatgca attattgggt gtacgtctga aaaaggcaa   4200
taaaacagat accattacta ggactttatt attttttgtaa gcatgttatc actggaacag   4260
atcatgcaat tattgcttac taatgcgtca attctttgct cattttttgct ttggtacctg   4320
agttgagcat atggtttctc gttttattc aggtatttca aggggcctga gcttcttgtt   4380
gatttgcaag attatgatta ttcttttggac atgtggagcc ttggttgcat gttttgctggg  4440
atggtatgtg tggctgtaaa aaatatcgcc tgtctaggtc aatgtctgga tatctaatgt   4500
actattgtat tgataataag tctgacgtct gaactcagtt aattgtatgc tatgatgcag   4560
atattccgca aggagccatt cttctatggt catgataacc atgatcaact tgtcaagatc   4620
gcaaaggtaa gtcccagttt gattctggcc tctcacattt ctcatgggaa aaaaaattgg   4680
tttggtatgc ctgataaaat gtttagttat gcaactcgtg ttttggactg gttggtatac   4740
atgttttact ttgtttctaa aaaaaattgc tgtttgtgct ccttttagct tagtactcat   4800
atgttattct gacatataag cagtgtgatg tcgtcaaaat aaattatgtt catttgtaaa   4860
ttgtgatttt tgaagttctt atttgttgct ctcgaactct tactaggacg gttattggca   4920
tttaaagatg ttttaagcat ccaataatgc ctcgagtgtg tgtcagcagt gttgattcgc   4980
ttgtcatcag ttgaaaacta agtacttttc cagcattatg ctattgatat cggactaagg   5040
cagatgtcat aatgtacttt gatatctatg caaattttat tcttgatctg ttttagtggt   5100
ttataaagt gcttattttg gaataacaat aaaacagcta tatgtgaaat attggtatct   5160
gatccatgtg ttttccccat cattctcagg tacttggaac agaagcacta aatgcttatt   5220
tgaacaagta ccatattgag cttgatcctc agcttgaagc tcttgttggg aggtacgttg   5280
ccatgctttt agatattggt tttgaacggg aagattcaga agtataacac ttacatatac   5340
atatgcaggc atagtagaaa accatggtcg aaattcatta atgctgataa ccaacatcta   5400
gtatctcctg aggtttgtca atggctcttg ctgtttccaa atcaacctta agataatgtt   5460
tgcttaacat catgcttgta catttgtagg ctgtagattt tcttgataag cttctacgtt   5520
atgatcacca agataggctc actgcacgtg aagctatgtg aagtctaccc cgacagataa   5580
tatttgttac attccaagaa gatactgatt tgtttgact ggatatttcc tatttatgta   5640
acagtattga ctgttcactg agattgttag tttattgctg aatatttag tatatatcct   5700
ccttttttagt cataagaatt acatcaatga tgtcataata gtactttcat cttcctatcc   5760
```

-continued

```
tatcacacct ctgttcaatt tttattttag gcatattctg tttcacttat tgctctgtat    5820
tatgacaata tcataaaaca ttttcctgac cctcaaccaa aaatagttgg caagttatgc    5880
atttgtatag gtacacttca actagggatg caagtggagc gggcaatcgg ttattttttg    5940
cccgtttatc tcaattctag ttcaattgtt gtaggtattt atgcaggtaa cgggattgct    6000
cactcgcatc gctaacttca acccaatata atttggcaaa tggtgcattt ggcaatagat    6060 agaaacccctt caaatttctc tgccacattg gcttttgtat gcaatgaaca acgtttcatc    6120
ttcacatagt atctggccag ttgtaggagg aacaaattgt tatttgatta ctcttggact    6180
tctcaaatta atgccataat catgaatact tgcaggcaca tccgtacttc ctccaagtga    6240
gagctgcaga aaatagcaga gcacgaccac aatgatcttg tgtacctgct aaaatgatga    6300
tccagctgat gatccacgac ggtactactt tgagtttgtg tgaacgatcg tggaatgtgc    6360
ttgtagcctt gtatttgtaa actgtaattc actccgttgg ttgcgtttga tgaatgccgt    6420
gacatgcaca taattattta tttctgtaat gtttaccat aacaacgatt aagatgcaac    6480
aggtacctgt atgactgcat gagccttgtt aagcttgttt cgaaatgagg ccgaagtgca    6540
tgtcttagct cggttcaaat tactaaaatt aactctagta gtaaatattg gggccaaaat    6600
ttggctgctt atttctccac taacttattt ggacctttaa cgggccatta aatatacaaa    6660
ccgaccattc atggcacagg taggcctcaa atgggcccat aaataggcct accatgagat    6720
ataatcaggc cttacatggg ccatcggttg gataagcggg gcctaaatgg accaaaccat    6780
ggattctcgg ggcgtaaatg cagcatccaa aattgggcgg tgaaggtacc gtgttctctc    6840
tccctgttct tttaagggtt gaaccgtgtt ataactcaca gaaggaaaaa tatcacgaaa    6900
tatttcgtcc tcatgttatg tcacaaattc                                    6930
```

<210> SEQ ID NO 3
<211> LENGTH: 1489
<212> TYPE: DNA
<213> ORGANISM: Oryza sativa (Kasalath)
<220> FEATURE:
<221> NAME/KEY: CDS
<222> LOCATION: (285)..(1283)

<400> SEQUENCE: 3

```
cgtcccacgc cgcctctatc tatctccacg tgaaataaaa aaaaaacaaa gctcccgaaa    60
atattctctc tccccacccc ccgaaaccct agcgcgacct cgccgccggc aatggccgca    120
tgaccgatgc gcctccgccg aggagccgcc cgcacccacc cagcagcagc gtcgccgtgc    180
ccgccgccgc ggcggcagtg atcgcagccg ccctcgcgtc ctccttcctc gccctgctgc    240
agccgccccg cgcgcccccg gtcgccgcgg gatccagggt cggc atg tcg aag gcg    296
                                                 Met Ser Lys Ala
                                                  1 agg gtc tac gcc gac gtc aac gtg ctg cgc ccc aag gag tac tgg gac    344
Arg Val Tyr Ala Asp Val Asn Val Leu Arg Pro Lys Glu Tyr Trp Asp
 5                  10                  15                  20 tac gag gcg ctc acc gtt caa tgg ggt gag cag gat gac tat gaa gtt    392
Tyr Glu Ala Leu Thr Val Gln Trp Gly Glu Gln Asp Asp Tyr Glu Val
                25                  30                  35 gtc agg aaa gtt gga aga ggt aaa tat agt gaa gtc ttt gaa ggc atc    440
Val Arg Lys Val Gly Arg Gly Lys Tyr Ser Glu Val Phe Glu Gly Ile
            40                  45                  50 aat gtt aac aac aat gag aaa tgc atc atc aag ata ctc aag cct gtg    488
Asn Val Asn Asn Asn Glu Lys Cys Ile Ile Lys Ile Leu Lys Pro Val
        55                  60                  65
```

```
aag aaa aag aag atc aaa agg gag att aaa ata ctt cag aat ctt tgt        536
Lys Lys Lys Lys Ile Lys Arg Glu Ile Lys Ile Leu Gln Asn Leu Cys
 70              75              80 gga ggt cca aac att gtg aag ctt ctt gat att gtc aga gat caa cat        584
Gly Gly Pro Asn Ile Val Lys Leu Leu Asp Ile Val Arg Asp Gln His
 85              90              95             100 tct aag act cct agc ttg atc ttt gaa tat gtc aac aat aca gac ttc        632
Ser Lys Thr Pro Ser Leu Ile Phe Glu Tyr Val Asn Asn Thr Asp Phe
                105             110             115 aaa gtg ctg tac ccc acg ttg aca gat tat gat atc cgc tac tac ata        680
Lys Val Leu Tyr Pro Thr Leu Thr Asp Tyr Asp Ile Arg Tyr Tyr Ile
            120             125             130 tat gag cta ctc aag gca tta gac tac tgc cat tca caa ggc att atg        728
Tyr Glu Leu Leu Lys Ala Leu Asp Tyr Cys His Ser Gln Gly Ile Met
        135             140             145 cat cga gat gtc aag ccc cac aat gtt atg ata gat cat gag ctc cga        776
His Arg Asp Val Lys Pro His Asn Val Met Ile Asp His Glu Leu Arg
    150             155             160 aaa ctt cga ttg ata gac tgg ggc ctg gct gag ttc tat cat cca ggg        824
Lys Leu Arg Leu Ile Asp Trp Gly Leu Ala Glu Phe Tyr His Pro Gly
165             170             175             180 aag gaa tat aat gtt cgt gtt gct tca agg tat ttc aag ggg cct gag        872
Lys Glu Tyr Asn Val Arg Val Ala Ser Arg Tyr Phe Lys Gly Pro Glu
                185             190             195 ctt ctt gtt gat ttg caa gat tat gat tat tct ttg gac atg tgg agc        920
Leu Leu Val Asp Leu Gln Asp Tyr Asp Tyr Ser Leu Asp Met Trp Ser
            200             205             210 ctt ggt tgc atg ttt gct ggg atg ata ttc cgc aag gag cca ttc ttc        968
Leu Gly Cys Met Phe Ala Gly Met Ile Phe Arg Lys Glu Pro Phe Phe
        215             220             225 tat ggt cat gat aac cat gat caa ctt gtc aag atc gca aag gta ctt       1016
Tyr Gly His Asp Asn His Asp Gln Leu Val Lys Ile Ala Lys Val Leu
    230             235             240 gga aca gaa gca cta aat gct tat ttg aac aag tac cat att gag ctt       1064
Gly Thr Glu Ala Leu Asn Ala Tyr Leu Asn Lys Tyr His Ile Glu Leu
245             250             255             260 gat cct cag ctt gaa gct ctt gtt ggg agg cat agt aga aaa cca tgg       1112
Asp Pro Gln Leu Glu Ala Leu Val Gly Arg His Ser Arg Lys Pro Trp
                265             270             275 tcg aaa ttc att aat gct gat aac caa cat cta gta tct cct gag gct       1160
Ser Lys Phe Ile Asn Ala Asp Asn Gln His Leu Val Ser Pro Glu Ala
            280             285             290 gta gat ttt ctt gat aag ctt cta cgt tat gat cac caa gat agg ctc       1208
Val Asp Phe Leu Asp Lys Leu Leu Arg Tyr Asp His Gln Asp Arg Leu
        295             300             305 act gca cgt gaa gct atg gca cat ccg tac ttc ctc caa gtg aga gct       1256
Thr Ala Arg Glu Ala Met Ala His Pro Tyr Phe Leu Gln Val Arg Ala
    310             315             320 gca gaa aat agc aga gca cga cca caa tgatcttgtg tacctgctaa             1303
Ala Glu Asn Ser Arg Ala Arg Pro Gln
325             330 aatgatgatc cagctgatga tccacgacgg tactactttg agtttgtgtg aacgatcgtg     1363
gaatgtgctt gtagccttgt atttgtaaac tgtaattcac tccgttggtt gcgtttgatg     1423
aatgccgtga catgcacata attatttatt tctgtaatgt tttaccataa caaaaaaaaa     1483
aaaaaa                                                                1489

<210> SEQ ID NO 4
```

-continued

<211> LENGTH: 90
<212> TYPE: PRT
<213> ORGANISM: Oryza sativa (Nipponbare)

<400> SEQUENCE: 4

Met Ser Lys Ala Arg Val Tyr Ala Asp Val Asn Val Leu Arg Pro Lys
 1               5                  10                  15

Glu Tyr Trp Asp Tyr Glu Ala Leu Thr Val Gln Trp Gly Glu Gln Asp
            20                  25                  30

Asp Tyr Glu Val Val Arg Lys Val Gly Arg Gly Lys Tyr Ser Glu Val
        35                  40                  45

Phe Glu Gly Ile Asn Val Asn Asn Glu Lys Cys Ile Ile Lys Ile
    50                  55                  60

Leu Lys Pro Val Lys Lys Lys Ile Lys Arg Glu Ile Lys Ile Leu
65                  70                  75                  80

Gln Asn Leu Cys Gly Gly Pro Asn Ile Val
            85                  90

<210> SEQ ID NO 5
<211> LENGTH: 6929
<212> TYPE: DNA
<213> ORGANISM: Oryza sativa (Nipponbare)

<400> SEQUENCE: 5

| | | | | | |
|---|---|---|---|---|---|
| cacactattg | gcctggcctt | agtgccagaa | cctgtttatt | tcttctgttt | tatagtctga | 60 |
| tgcattttg | ttaatggaaa | tggagggcct | ttttcccttc | gataaaaaaa | atgtataaga | 120 |
| ttattagtta | attatggtag | tattgaaaaa | tataccacga | taaaaaaact | taaaatcaaa | 180 |
| ttaaaattaa | gtttcaacat | ttatatttta | gctacgggtg | ataagtcaaa | acacaaacaa | 240 |
| cggtctttgt | acgtaagtct | ttttcaaaac | ttgtggtaaa | cattctccgt | tcagttatta | 300 |
| atatttgatg | tttaggacaa | gatccgatca | aacttctaaa | attctaacaa | atcaattcta | 360 |
| tattaaatta | agtttatgaa | gcgctataag | cttgtgattt | tatgatagca | cttgttgaga | 420 |
| taaatatatg | tatatctttt | atcttatctt | taaactaagt | agaggtattt | gttaaattat | 480 |
| tgatgatcag | aaatttaaaa | agttcgacca | tatcttgtac | tagtactaaa | cgtaaaatat | 540 |
| ttttgactaa | aggaagtaat | taaaatttaa | gaggcaaaat | tacgtgtgaa | tttgagaaga | 600 |
| cttccaattc | aacagctcaa | tgatcgggac | acattcttaa | aaagaaaaa | aagaaacaa | 660 |
| aaaagatccg | gacacgcatg | cgcaaatgga | gctttcatag | gcagaaggcg | taatcaactg | 720 |
| gaaggcgtct | tctcctggag | ggaaaggtcg | ggcccacgta | agggaacaaa | accacctgtc | 780 |
| agtgaccaaa | agccagcaga | ttccagagtc | gccgtcccac | gccgcctcta | tctatctcca | 840 |
| cgtgaaataa | aaaaaaaaca | aagctcccga | aaatattctc | tctccccac | ccccgaaacc | 900 |
| ctagcgcgac | ctcgccgccg | gcaatggccg | catgaccgat | gcgcctccgc | cgaggagccg | 960 |
| cccgcaccca | cccagcagca | gcgtcgccgt | gcccgccgcc | gcggcggcag | tgatcgcagc | 1020 |
| cgccctcgcg | tcctccttcc | tcgccctgct | gcagccgccc | cggcgcgccc | cggtcgccgc | 1080 |
| gggatccagg | gtcggcatgt | cgaaggcgag | ggtctacgcc | gacgtcaacg | tgctgcgccc | 1140 |
| caaggagtac | tgggactacg | aggcgctcac | cgttcaatgg | gggtaggtag | cacagccagc | 1200 |
| cagctgacgt | caccttcctg | agccccctga | tcagcggccg | tagcttgtat | tctccagatt | 1260 |
| tagttcgcga | tccgtatccc | gtacacctgg | gctgggtttg | cttattggga | ttaggttgga | 1320 |
| ttattgggtt | atgcgtaggt | ttgcttgtgc | ctgtagattt | tggttttggt | cagggaattg | 1380 |
| ggaattatt | gtagcttgaa | ggttagattg | aattgcttct | gtttctatta | ggacgaactc | 1440 |

-continued

```
aataccgaag actgctttgg tagttttaca tgtttgtact ataggagtag gggacacatg   1500
tttaccgaat ggttgaagaa attgttatga atttgcaagg ttatgatttt aattttggaa   1560
tcaatctcac tatatcttcc ttttaaagtt gatactagtg ttgttcagtt aagagccttt   1620
gtttgattgt gaatggcaag ctgtaggtat tgatcctatt tttgttgggg ataaaatcta   1680
agttaaggca aaattaggca gttttatgtt taatcattgg aacaaagtaa gttggtgatg   1740
ggtttctggg tgtttctttt gcatcatctg ataaccaaga ttgatgagta aagcataact   1800
tggtagtata gtgctttggg cctaatcttc tttagcactg aacattcacc aagttctatg   1860
cttttatgta atctcaaatt taacattgtg ttttccttca ctcaccctag aatatactac   1920
ctgaaagcaa tcaatgaaat caaatataac ttcgtttcta cctatatgat tgtaacatgc   1980
tgagtaatat ggtgccaaac aactcaacac atataatact gtccttaaca acccatcttc   2040 ttttcccctgt agaagttaca gccctagtat attctgtaca tgtcatgcta cctagatgac   2100
agttgaggcc tggtaggagt gtgcttgttt aattttggta ctccaaaagt gcactgtttt   2160
tctcaatctg actctgttac cagttgtgtt tcctctagat gtattcctta tctatggtga   2220
attattaaat aagttgtctg gtgacaaaaa aaaagaaaa ataaagaag agatgaacaa    2280 tatgtagctc attgatgatc ccttgtctgc ttgaaacttta tgagaaacta tagaaagcag   2340
tggtgttttc cctgacctga tgttaaatac ttgttaagaa ttgagctttc ttcgaagttt   2400
gttcagttta cacaccaaca ctaagaattg ccatatatct cccatctttt gtccatttaa    2460
ttcttgttac ctcaagtcat tgagggacct ggcagcatgt tatgacttac acaatacctc   2520
gctaactatt atggtgcatc tttaacagtg agcaggatga ctatgaagtt gtcaggaaag   2580
ttggaagagg taaatatagt gaagtctttg aaggcatcaa tgttaacaac aatgagaaat   2640
gcatcatcaa gatactcaag cctgtgaaga aaagaaggt atttaattga tcttattgac    2700 tgttttttt aattgctagt gttgaagttc ttaacctacc tttcatatgt ttgaacagat     2760 caaagggag attaaaatac ttcagaatct ttgtggaggt ccaaacattg tgtagcttct    2820
tgatattgtc agagatcaac attctaagac tcctagcttg atctttgaat atgtcaacaa    2880
tacagacttc aaagtgctgt acccacgtt gacagattat gatatccgct actacatata    2940
tgagctactc aaggtcttca ttgagccttc attgtcatcc ctatttattt actctattca    3000
gtaaaacatc ctgttctgtg gatctgtaga atgatgtatc tcttatagaa attgttttca   3060
caattacttt cctattatgt gaagatccaa ctaaacacac ttgtaatata tcctagacaa   3120
atatcaccat tctcactgct tgcaagttgc aacatatctt taattattta tgtatatatg   3180
aacttgatta ttttctaaag ttacatggct taaaacttgt cacaatctca agcagtttat   3240
ggatcagttt tgttttgagt tttaattata gtagcatctt gcacttcata atgtacagat   3300
gacaaaagaa ttcctgaatt gcatatgtgc tataatggtt tatgatctgg gattttgaag   3360
agaagtgtcg ttttatacat ttctaagttc agcactatgt tggtgttaag aattcagcca   3420
tcaatgggca tcttaacgta tgtgctaggt catgccttct atccatgggt aataaactgt    3480
taacacacag tgtgtgtttt tcatatcgat attcttagcc aagaacagta gcatcatttg   3540
cccttaatcc tgtgtgttaa gtttgtttaa agaatctagt tgattttctt tacaatattt    3600
tccttctgtt tatggcccca ggcattagac tactgccatt cacaaggcat tatgcatcga   3660
gatgtcaagc cccacaatgt tatgatagat catgagctcc gaaaacttcg attgatagac   3720
tggggcctgg ctgagttcta tcatccaggg aaggaatata atgttcgtgt tgcttcaagg   3780
```

-continued

```
ttggtgtagt tacaagcaaa ctacttgttt ggttatgatt ttcttgcttt tttattgaat    3840
tggattgcac cctgataatc acttgaatca tgagaggaag ctaacttaag aaggtagcat    3900
ccctgttttg cagtttgttt gctaacttgg ctctagaagc aatacgtgaa ccgataaatt    3960
acttggtttg aattcactgc tactgttgaa gtctgaattg cctagtggtc cttttgcaac    4020
attaatgtta cgaaatgctg aaagttaagc aatgaagctg tttacccttaa acaactaag    4080 tttacgtctg aaaaaaggc aataaaacag ataccattac tagccccttta ttattttgt    4140 aagcatgtta tcactggagt atatcatgca attattgggt gtacgtctga aaaaaggcaa    4200
taaaacagat accattacta ggactttatt attttttgtaa gcatgttatc actggaatag    4260
atcatgcaat tattgcttac taatgcgtca attctttgct cattttttgct ttggtacctg    4320 agttgagcat atggtttctc gttttttattc aggtatttca aggggcctga gcttcttgtt    4380
gatttgcaag attatgatta ttcttttggac atgtggagcc ttggttgcat gtttgctggg    4440
atggtatgtg tggctgtaaa aaatatcgcc tgtctaggtc aatgtctgga tatctaatgt    4500
actattgtat tgataataag tctgacgtct gaactcagtt aactgtatgc tatgatgcag    4560
atattccgca aggagccatt cttctatggt catgataacc atgatcaact tgtcaagatc    4620
gcaaaggtaa gtcccagttt gattctggcc tctcacatttt ctcaagggaa aaaaaatggt    4680
ttggtatgcc tgataaaatg tttagttatg caactcgtgt tttggactgg ttggtataca    4740
tgttttactt tgtttctaaa aaaaattgct gtttgtgctc cttttagctt agtactcata    4800
tgttattctg acatataagc agtgtgatgt cgtcaaaata aattatgttc atttgtaaat    4860
tgtgattttt gaagttctta tttgttgctc tcgaactctt actaggacgg ttattggcat    4920
ttaaagatgt tttaagcatc caataatgcc tcgagtgtgt gtcagcagtg ttgattcgct    4980
tgtcatcagt tgaaaactaa gtacttttcc agcattatgc tattgatatc ggactaaggc    5040
agatgtcata atgtactttg atatctatgc aaattttatt cttgatctgt tttagtggtt    5100
tatataagtg cttattttgg aataacaata aaacagctat atgtgaaata ttggtatctg    5160
atccatgtgt tttccccatc attctcaggt acttggaaca gaagcactaa atgcttattt    5220
gaacaagtac catattgagc ttgatcctca gcttgaagct cttgttggga ggtacgttgc    5280
catgctttta gatattggtt ttgaacggga agattcagaa gtataacact tacatataca    5340
tatgcaggca tagtagaaaa ccatggtcga aattcattaa tgctgataac caacatctag    5400
tatctcctga ggtttgtcaa tggctcttgc tgtttccaaa tcaaccttaa gataatgttt    5460
gcttaacatc atgcttgtac atttgtaggc tgtagatttt cttgataagc ttctacgtta    5520
tgatcaccaa gataggctca ctgcacgtga agctatggta agtctacccc gacagataat    5580
atttgttaca ttccaagaag atactgattt tgtttgactg gatatttcct atttatgtaa    5640
cagtattgac tgttcactga gattgttagt ttattgctga atattttagt atatatcctc    5700 cttttttagtc ataagaatta catcaatgat gtcataatag tactttcatc ttcctatcct    5760
atcacacctc tgttcaattt ttattttagg catattctgt ttcacttatt gctctgtatt    5820
atgacaatat cataaaacat tttcctgacc ctcaaccaaa aatagttggc aagttatgca    5880
tttgtatagg tacacttcaa ctagggatgc aagtggagcg ggcaatcggt tattttttgc    5940
ctgtttatct caattctagt tcaattgttg taggtattta tgcaggtaac aggattgctt    6000
actcgcatcg ctaacttcaa cccaatataa tttggcaaat ggtgcatttg gcaatagata    6060
gaaacccttc aaatttctct gccacattgg cttttgtatg caatgaacaa cgtttcatct    6120
tcacatagta tctggccagt tgtaggagga acaaattgtt atttgattac tcttggactt    6180
```

```
ctcaaattaa tgccataatc atgaatactt gcaggcacat ccgtacttcc tccaagtgag      6240
agctgcagaa aatagcagag cacgaccaca atgatcttgt gtacctgcta aaatgatgat      6300
ccagctgatg atccacgacg gtactacttt gagtttgtgt gaacgatcgt ggaatgtgct      6360
tgtagccttg catttgtaaa ctgtaattca ctccgttggt tgcgtttgat gaatgccgtg      6420
acatgcacat aattatttat ttctgtaatg ttttaccata acaacgatta agatgcaaca      6480
ggtacctgta tgacagcatg agccttgtta agcttgtttc gaatgaggc cgaagtgcat       6540 gtcttagctc ggttcaaatt actaaaatta actctagtag taaatattgg ggccaaaatt      6600
tggctgctta tttcaccact aacttatttg gacctttaac gggccattaa atatacaaac      6660
cgaccattca tggcacaggt aggcctcaaa tgggcccata ataggccta ccatgagata       6720 taatcaggcc ttacatgggc catcggttgg ataagcgggg cctaaatgga ccaaaccatg      6780
gattctcggg gcgtaaatgc agcatccaaa attgggcggt gaaggtaccg tgttctctct      6840
ccctgttctt ttaagggttg aaccgtgtta taactcacag aaggaaaaat atcacgaaat      6900
atttcgtcct catgttatgt cacaaattc                                       6929

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
gcaaaatgcc actttgtggc                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
aacttacgct caaatcaaaa                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
tgttgccctc attatctgct                                                   20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
ggaggtcgga gtaaaggaaa                                                   20
```

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
agcactcaaa aacaccaagc                                                     20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
aacaaagata caaacagcac                                                     20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
cttgatcctc agcttgaagc t                                                   21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
tgcaaggcta caagcacatt c                                                   21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
tcgtcgcgct catagctaga                                                     20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
acttcctcgc tatgccacag                                                     20
```

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
gcccataatg atacgatata ct                                            22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
tggtggtggt tgctgttcga                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 18
ctgcaagttc aagccgatca                                               20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 19
ttgcaattgg ctaagcaaga c                                             21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 20
acctggcagc atgttatgac                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 21
ctacagatcc acagaacagg                                               20

<210> SEQ ID NO 22

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 22
ctttgtggag gtccaaacat tgtc                                              24

<210> SEQ ID NO 23
<211> LENGTH: 333
<212> TYPE: PRT
<213> ORGANISM: Oryza sp.

<400> SEQUENCE: 23
```

| Met | Ser | Lys | Ala | Arg | Val | Tyr | Ala | Asp | Val | Asn | Val | Leu | Arg | Pro | Lys |
|---|---|---|---|---|---|---|---|---|---|---|---|---|---|---|---|
| 1 | | | | 5 | | | | | 10 | | | | | 15 | |

| Glu | Tyr | Trp | Asp | Tyr | Glu | Ala | Leu | Thr | Val | Gln | Trp | Gly | Glu | Gln | Asp |
|---|---|---|---|---|---|---|---|---|---|---|---|---|---|---|---|
| | | | 20 | | | | | 25 | | | | | 30 | | |

| Asp | Tyr | Glu | Val | Val | Arg | Lys | Val | Gly | Arg | Gly | Lys | Tyr | Ser | Glu | Val |
|---|---|---|---|---|---|---|---|---|---|---|---|---|---|---|---|
| | | 35 | | | | | 40 | | | | | 45 | | | |

| Phe | Glu | Gly | Ile | Asn | Val | Asn | Asn | Glu | Lys | Cys | Ile | Ile | Lys | Ile |
|---|---|---|---|---|---|---|---|---|---|---|---|---|---|---|
| 50 | | | | | 55 | | | | | 60 | | | | |

| Leu | Lys | Pro | Val | Lys | Lys | Lys | Ile | Lys | Arg | Glu | Ile | Lys | Ile | Leu |
|---|---|---|---|---|---|---|---|---|---|---|---|---|---|---|
| 65 | | | | 70 | | | | | 75 | | | | | 80 |

| Gln | Asn | Leu | Cys | Gly | Gly | Pro | Asn | Ile | Val | Lys | Leu | Leu | Asp | Ile | Val |
|---|---|---|---|---|---|---|---|---|---|---|---|---|---|---|---|
| | | | | 85 | | | | | 90 | | | | | 95 | |

| Arg | Asp | Gln | His | Ser | Lys | Thr | Pro | Ser | Leu | Ile | Phe | Glu | Tyr | Val | Asn |
|---|---|---|---|---|---|---|---|---|---|---|---|---|---|---|---|
| | | | | 100 | | | | | 105 | | | | | 110 | |

| Asn | Thr | Asp | Phe | Lys | Val | Leu | Tyr | Pro | Thr | Leu | Thr | Asp | Tyr | Asp | Ile |
|---|---|---|---|---|---|---|---|---|---|---|---|---|---|---|---|
| | | | 115 | | | | | 120 | | | | | 125 | | |

| Arg | Tyr | Tyr | Ile | Tyr | Glu | Leu | Leu | Lys | Ala | Leu | Asp | Tyr | Cys | His | Ser |
|---|---|---|---|---|---|---|---|---|---|---|---|---|---|---|---|
| | | 130 | | | | | 135 | | | | | 140 | | | |

| Gln | Gly | Ile | Met | His | Arg | Asp | Val | Lys | Pro | His | Asn | Val | Met | Ile | Asp |
|---|---|---|---|---|---|---|---|---|---|---|---|---|---|---|---|
| 145 | | | | | 150 | | | | | 155 | | | | | 160 |

| His | Glu | Leu | Arg | Lys | Leu | Arg | Leu | Ile | Asp | Trp | Gly | Leu | Ala | Glu | Phe |
|---|---|---|---|---|---|---|---|---|---|---|---|---|---|---|---|
| | | | | 165 | | | | | 170 | | | | | 175 | |

| Tyr | His | Pro | Gly | Lys | Glu | Tyr | Asn | Val | Arg | Val | Ala | Ser | Arg | Tyr | Phe |
|---|---|---|---|---|---|---|---|---|---|---|---|---|---|---|---|
| | | | 180 | | | | | 185 | | | | | 190 | | |

| Lys | Gly | Pro | Glu | Leu | Leu | Val | Asp | Leu | Gln | Asp | Tyr | Asp | Tyr | Ser | Leu |
|---|---|---|---|---|---|---|---|---|---|---|---|---|---|---|---|
| | | 195 | | | | | 200 | | | | | 205 | | | |

| Asp | Met | Trp | Ser | Leu | Gly | Cys | Met | Phe | Ala | Gly | Met | Ile | Phe | Arg | Lys |
|---|---|---|---|---|---|---|---|---|---|---|---|---|---|---|---|
| 210 | | | | | 215 | | | | | 220 | | | | | |

| Glu | Pro | Phe | Phe | Tyr | Gly | His | Asp | Asn | His | Asp | Gln | Leu | Val | Lys | Ile |
|---|---|---|---|---|---|---|---|---|---|---|---|---|---|---|---|
| 225 | | | | | 230 | | | | | 235 | | | | | 240 |

| Ala | Lys | Val | Leu | Gly | Thr | Glu | Ala | Leu | Asn | Ala | Tyr | Leu | Asn | Lys | Tyr |
|---|---|---|---|---|---|---|---|---|---|---|---|---|---|---|---|
| | | | | 245 | | | | | 250 | | | | | 255 | |

| His | Ile | Glu | Leu | Asp | Pro | Gln | Leu | Glu | Ala | Leu | Val | Gly | Arg | His | Ser |
|---|---|---|---|---|---|---|---|---|---|---|---|---|---|---|---|
| | | | | 260 | | | | | 265 | | | | | 270 | |

| Arg | Lys | Pro | Trp | Ser | Lys | Phe | Ile | Asn | Ala | Asp | Asn | Gln | His | Leu | Val |
|---|---|---|---|---|---|---|---|---|---|---|---|---|---|---|---|
| | | 275 | | | | | 280 | | | | | 285 | | | |

| Ser | Pro | Glu | Ala | Val | Asp | Phe | Leu | Asp | Lys | Leu | Leu | Arg | Tyr | Asp | His |
|---|---|---|---|---|---|---|---|---|---|---|---|---|---|---|---|
| | | 290 | | | | | 295 | | | | | 300 | | | |

| Gln | Asp | Arg | Leu | Thr | Ala | Arg | Glu | Ala | Met | Ala | His | Pro | Tyr | Phe | Leu |
|---|---|---|---|---|---|---|---|---|---|---|---|---|---|---|---|
| 305 | | | | | 310 | | | | | 315 | | | | | 320 |

```
Gln Val Arg Ala Ala Glu Asn Ser Arg Ala Arg Pro Gln
            325                 330
```

`<210>` SEQ ID NO 24
`<211>` LENGTH: 332
`<212>` TYPE: PRT
`<213>` ORGANISM: Zea sp.

`<400>` SEQUENCE: 24

```
Met Ser Lys Ala Arg Val Tyr Ala Asp Val Asn Val Leu Arg Pro Lys
 1               5                  10                  15
Glu Tyr Trp Asp Tyr Glu Ala Leu Thr Val Gln Trp Gly Glu Gln Asp
             20                  25                  30
Asp Tyr Glu Val Val Arg Lys Val Gly Arg Gly Lys Tyr Ser Glu Val
         35                  40                  45
Phe Glu Gly Ile Asn Val Asn Asn Asn Glu Lys Cys Ile Ile Lys Ile
     50                  55                  60
Leu Lys Pro Val Lys Lys Lys Lys Ile Lys Arg Glu Ile Lys Ile Leu
 65                  70                  75                  80
Gln Asn Leu Cys Gly Gly Pro Asn Ile Val Lys Leu Leu Asp Ile Val
                 85                  90                  95
Arg Asp Gln His Ser Lys Thr Pro Ser Leu Ile Phe Glu Tyr Val Asn
             100                 105                 110
Asn Thr Asp Phe Lys Val Leu Tyr Pro Thr Leu Thr Asp Tyr Asp Ile
         115                 120                 125
Arg Tyr Tyr Ile Tyr Glu Leu Leu Lys Ala Leu Asp Tyr Cys His Ser
     130                 135                 140
Gln Gly Ile Met His Arg Asp Val Lys Pro His Asn Val Met Ile Asp
145                 150                 155                 160
His Glu Leu Arg Lys Leu Arg Leu Ile Asp Trp Gly Leu Ala Glu Phe
                 165                 170                 175
Tyr His Pro Gly Lys Glu Tyr Asn Val Arg Val Ala Ser Arg Tyr Phe
             180                 185                 190
Lys Gly Pro Glu Leu Leu Val Asp Leu Gln Asp Tyr Asp Tyr Ser Leu
         195                 200                 205
Asp Met Trp Ser Leu Gly Cys Met Phe Ala Gly Met Ile Phe Arg Lys
     210                 215                 220
Glu Pro Phe Phe Tyr Gly His Asp Asn His Asp Gln Leu Val Lys Ile
225                 230                 235                 240
Ala Lys Val Leu Gly Thr Asp Gly Leu Asn Val Tyr Leu Asn Lys Tyr
                 245                 250                 255
Arg Ile Glu Leu Asp Pro Gln Leu Glu Ala Leu Val Gly Arg His Ser
             260                 265                 270
Arg Lys Pro Trp Leu Lys Phe Met Asn Ala Asp Asn Gln His Leu Val
         275                 280                 285
Ser Pro Glu Ala Ile Asp Phe Leu Asp Lys Leu Leu Arg Tyr Asp His
     290                 295                 300
Gln Glu Arg Leu Thr Ala Leu Glu Ala Met Thr His Pro Tyr Phe Gln
305                 310                 315                 320
Gln Val Arg Ala Ala Glu Asn Ser Arg Thr Arg Ala
                 325                 330
```

`<210>` SEQ ID NO 25
`<211>` LENGTH: 333
`<212>` TYPE: PRT
`<213>` ORGANISM: Arabidopsis sp.

```
<400> SEQUENCE: 25

Met Ser Lys Ala Arg Val Tyr Thr Asp Val Asn Val Ile Arg Pro Lys
1               5                   10                  15

Asp Tyr Trp Asp Tyr Glu Ser Leu Asn Val Gln Trp Gly Glu Gln Asp
            20                  25                  30

Asp Tyr Glu Val Val Arg Lys Val Gly Arg Gly Lys Tyr Ser Glu Val
        35                  40                  45

Phe Glu Gly Ile Asn Met Asn Asn Asn Glu Lys Cys Ile Ile Lys Ile
    50                  55                  60

Leu Lys Pro Val Lys Lys Glu Ile Arg Arg Glu Ile Lys Ile Leu
65                  70                  75                  80

Gln Asn Leu Cys Gly Gly Pro Asn Ile Val Lys Leu Leu Asp Val Val
                85                  90                  95

Arg Asp Gln His Ser Lys Thr Pro Ser Leu Ile Phe Glu Tyr Val Asn
            100                 105                 110

Ser Thr Asp Phe Lys Val Leu Tyr Pro Thr Leu Thr Asp Tyr Asp Ile
        115                 120                 125

Arg Tyr Tyr Ile Tyr Glu Leu Leu Lys Ala Leu Asp Phe Cys His Ser
    130                 135                 140

Gln Gly Ile Met His Arg Asp Val Lys Pro His Asn Val Met Ile Asp
145                 150                 155                 160

His Gly Leu Arg Lys Leu Arg Leu Ile Asp Trp Gly Leu Ala Glu Phe
                165                 170                 175

Tyr His Pro Gly Lys Glu Tyr Asn Val Arg Val Ala Ser Arg Tyr Phe
            180                 185                 190

Lys Gly Pro Glu Leu Leu Val Asp Leu Gln Asp Tyr Asp Tyr Ser Leu
        195                 200                 205

Asp Met Trp Ser Leu Gly Cys Met Phe Ala Gly Met Ile Phe Arg Lys
    210                 215                 220

Glu Pro Phe Phe Tyr Gly His Asp Asn Gln Asp Gln Leu Val Lys Ile
225                 230                 235                 240

Ala Lys Val Leu Gly Thr Asp Glu Leu Asn Ala Tyr Leu Asn Lys Tyr
                245                 250                 255

Gln Leu Glu Leu Asp Thr Gln Leu Glu Ala Leu Val Gly Arg His Ser
            260                 265                 270

Arg Lys Pro Trp Ser Lys Phe Ile Asn Ala Asp Asn Arg His Leu Val
        275                 280                 285

Ser Pro Glu Ala Ile Asp Tyr Leu Asp Lys Leu Leu Arg Tyr Asp His
    290                 295                 300

Gln Asp Arg Leu Thr Ala Lys Glu Ala Met Ala His Pro Tyr Phe Ala
305                 310                 315                 320

Gln Val Arg Ala Ala Glu Ser Ser Arg Met Arg Thr Gln
                325                 330

<210> SEQ ID NO 26
<211> LENGTH: 391
<212> TYPE: PRT
<213> ORGANISM: Homo sapiens

<400> SEQUENCE: 26

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30
```

```
Trp Gly Asn Gln Asp Asp Tyr Gln Leu Val Arg Lys Leu Gly Arg Gly
         35                  40                  45

Lys Tyr Ser Glu Val Phe Glu Ala Ile Asn Ile Thr Asn Asn Glu Lys
 50                  55                  60

Val Val Val Lys Ile Leu Lys Pro Val Lys Lys Lys Ile Lys Arg
 65                  70                  75                  80

Glu Ile Lys Ile Leu Glu Asn Leu Arg Gly Gly Pro Asn Ile Ile Thr
                 85                  90                  95

Leu Ala Asp Ile Val Lys Asp Pro Val Ser Arg Thr Pro Ala Leu Val
                100                 105                 110

Phe Glu His Val Asn Asn Thr Asp Phe Lys Gln Leu Tyr Gln Thr Leu
                115                 120                 125

Thr Asp Tyr Asp Ile Arg Phe Tyr Met Tyr Glu Ile Leu Lys Ala Leu
130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
                180                 185                 190

Ala Ser Arg Tyr Phe Lys Gly Pro Glu Leu Leu Val Asp Tyr Gln Met
            195                 200                 205

Tyr Asp Tyr Ser Leu Asp Met Trp Ser Leu Gly Cys Met Leu Ala Ser
        210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
                260                 265                 270

Leu Gly Arg His Ser Arg Lys Arg Trp Glu Arg Phe Val His Ser Glu
            275                 280                 285

Asn Gln His Leu Val Ser Pro Glu Ala Leu Asp Phe Leu Asp Lys Leu
        290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
                340                 345                 350

Ser Gly Ile Ser Ser Val Pro Thr Pro Ser Pro Leu Gly Pro Leu Ala
            355                 360                 365

Gly Ser Pro Val Ile Ala Ala Asn Pro Leu Gly Met Pro Val Pro
370                 375                 380

Ala Ala Ala Gly Ala Gln Gln
385                 390

<210> SEQ ID NO 27
<211> LENGTH: 336
<212> TYPE: PRT
<213> ORGANISM: Drosophila sp.

<400> SEQUENCE: 27

Met Thr Leu Pro Ser Ala Ala Arg Val Tyr Thr Asp Val Asn Ala His
 1               5                  10                  15
```

```
Lys Pro Asp Glu Tyr Trp Asp Tyr Glu Asn Tyr Val Val Asp Trp Gly
            20                  25                  30

Asn Gln Asp Asp Tyr Gln Leu Val Arg Lys Leu Gly Arg Gly Lys Tyr
            35                  40                  45

Ser Glu Val Phe Glu Ala Ile Asn Ile Thr Thr Glu Lys Cys Val
 50                  55                  60

Val Lys Ile Leu Lys Pro Val Lys Lys Lys Ile Lys Arg Glu Ile
 65              70                  75                  80

Lys Ile Leu Glu Asn Leu Arg Gly Gly Thr Asn Ile Ile Thr Leu Leu
                85                  90                  95

Ala Val Val Lys Asp Pro Val Ser Arg Thr Pro Ala Leu Ile Phe Glu
            100                 105                 110

His Val Asn Asn Thr Asp Phe Lys Gln Leu Tyr Gln Thr Leu Thr Asp
            115                 120                 125

Tyr Glu Ile Arg Tyr Tyr Leu Phe Glu Leu Leu Lys Ala Leu Asp Tyr
    130                 135                 140

Cys His Ser Met Gly Ile Met His Arg Asp Val Lys Pro His Asn Val
145                 150                 155                 160

Met Ile Asp His Glu Asn Arg Lys Leu Arg Leu Ile Asp Trp Gly Leu
                165                 170                 175

Ala Glu Phe Tyr His Pro Gly Gln Glu Tyr Asn Val Arg Val Ala Ser
            180                 185                 190

Arg Tyr Phe Lys Gly Pro Glu Leu Leu Val Asp Tyr Gln Met Tyr Asp
    195                 200                 205

Tyr Ser Leu Asp Met Trp Ser Leu Gly Cys Met Leu Ala Ser Met Ile
    210                 215                 220

Phe Arg Lys Glu Pro Phe Phe His Gly His Asp Asn Tyr Asp Gln Leu
225                 230                 235                 240

Val Arg Ile Ala Lys Val Leu Gly Thr Glu Glu Leu Tyr Ala Tyr Leu
            245                 250                 255

Asp Lys Tyr Asn Ile Asp Leu Asp Pro Arg Phe His Asp Ile Leu Gln
            260                 265                 270

Arg His Ser Arg Lys Arg Trp Glu Arg Phe Val His Ser Asp Asn Gln
    275                 280                 285

His Leu Val Ser Pro Glu Ala Leu Asp Phe Leu Asp Lys Leu Leu Arg
    290                 295                 300

Tyr Asp His Val Asp Arg Leu Thr Ala Arg Glu Ala Met Ala His Pro
305                 310                 315                 320

Tyr Phe Leu Pro Ile Val Asn Gly Gln Met Asn Pro Asn Asn Gln Gln
                325                 330                 335

<210> SEQ ID NO 28
<211> LENGTH: 360
<212> TYPE: PRT
<213> ORGANISM: Rhabdias sp.

<400> SEQUENCE: 28

Met Pro Pro Ile Pro Ser Arg Ala Arg Val Tyr Ala Glu Val Asn Pro
 1               5                  10                  15

Ser Arg Pro Arg Glu Tyr Trp Asp Tyr Glu Ala His Met Ile Glu Trp
            20                  25                  30

Gly Gln Ile Asp Asp Tyr Gln Leu Val Arg Lys Leu Gly Arg Gly Lys
            35                  40                  45

Tyr Ser Glu Val Phe Glu Gly Phe Lys Met Ser Thr Asp Glu Lys Val
```

-continued

```
                50                     55                     60
Val Val Lys Ile Leu Lys Pro Val Lys Lys Lys Ile Lys Arg Glu
 65              70                  75                    80

Ile Lys Ile Leu Glu Asn Leu Arg Gly Gly Thr Asn Ile Ile Thr Leu
                 85                  90                   95

Leu Asp Val Val Lys Asp Pro Ile Ser Arg Thr Pro Ala Leu Ile Phe
                100                 105                 110

Glu His Val Asn Asn Ser Asp Phe Lys Gln Leu Tyr Gln Thr Leu Ser
            115                 120                 125

Asp Tyr Asp Ile Arg Tyr Tyr Leu Tyr Glu Leu Leu Lys Ala Leu Asp
        130                 135                 140

Phe Cys His Ser Gln Gly Ile Met His Arg Asp Val Lys Pro His Asn
145                 150                 155                 160

Val Met Ile Asp Ala Glu Lys Arg Glu Leu Arg Leu Ile Asp Trp Gly
                165                 170                 175

Leu Ala Glu Phe Tyr His Pro Arg Gln Asp Tyr Asn Val Arg Val Ala
            180                 185                 190

Ser Arg Tyr Phe Lys Gly Pro Glu Leu Leu Val Asp Tyr Gln Cys Tyr
        195                 200                 205

Asp Tyr Ser Leu Asp Met Trp Ser Leu Gly Gly Met Leu Ala Ser Met
    210                 215                 220

Ile Phe Arg Lys Glu Pro Phe Phe His Gly His Asp Asn Tyr Asp Gln
225                 230                 235                 240

Leu Val Arg Ile Ala Lys Val Leu Gly Thr Asp Glu Leu Tyr Glu Tyr
                245                 250                 255

Ile Ala Arg Tyr His Ile Asp Leu Asp Pro Arg Phe Asn Asp Ile Leu
            260                 265                 270

Gly Arg His Ser Arg Lys Arg Trp Glu Arg Phe Ile His Ala Glu Asn
        275                 280                 285

Gln His Leu Val Thr Pro Glu Ala Leu Asp Phe Leu Asp Lys Leu Leu
290                 295                 300

Arg Tyr Asp His Ala Glu Arg Leu Thr Ala Gln Glu Ala Met Gly His
305                 310                 315                 320

Glu Tyr Phe Arg Pro Val Val Glu Ala His Ala Arg Ala Asn Gly Thr
                325                 330                 335

Glu Gln Ala Asp Gly Gln Gly Ala Ser Asn Ser Ala Ser Ser Gln Ser
            340                 345                 350

Ser Asp Ala Lys Ile Asp Gly Ala
        355                 360
```